(12) United States Patent
Wang et al.

(10) Patent No.: US 6,764,998 B1
(45) Date of Patent: Jul. 20, 2004

(54) 6,11-4C-BICYCLIC 9A-AZALIDE DERIVATIVES

(75) Inventors: Guoqiang Wang, Belmont, MA (US); Yat Sun Or, Watertown, MA (US); Ly Tam Phan, Malden, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 10/464,188

(22) Filed: Jun. 18, 2003

(51) Int. Cl.[7] .................... A61K 31/70; C07H 17/08
(52) U.S. Cl. .................. 514/29; 536/7.2; 536/7.3; 536/7.4
(58) Field of Search ................ 514/29; 536/7.2, 536/7.3, 7.4

(56) References Cited

U.S. PATENT DOCUMENTS

| | | | |
|---|---|---|---|
| 4,990,602 A | 2/1991 | Morimoto et al. | 536/7.4 |
| 5,403,923 A | 4/1995 | Kashimura et al. | 536/7.4 |
| 5,444,051 A | 8/1995 | Agouridas et al. | 514/29 |
| 5,527,780 A | 6/1996 | Agouridas et al. | 514/29 |
| 5,631,355 A | 5/1997 | Asaka et al. | 536/7.4 |
| 5,866,549 A | 2/1999 | Or et al. | 514/29 |
| 5,969,161 A | 10/1999 | Bonnet et al. | 549/271 |
| 6,046,171 A * | 4/2000 | Or et al. | 514/29 |
| 6,124,269 A | 9/2000 | Phan et al. | 514/29 |
| 6,399,582 B1 | 6/2002 | Hlasta et al. | 514/29 |

FOREIGN PATENT DOCUMENTS

| | | | |
|---|---|---|---|
| WO | WO 01/14397 | 3/2001 | C07H/17/08 |
| WO | WO 03/042228 | 5/2003 | C07H/17/08 |

OTHER PUBLICATIONS

Bright, et al. "Synthesis, In Vitro and In Vivo Activity of Novel 9–Deoxo–9a–Aza–9a–Homoerythromycin A Derivatives; A New Class of Macrolide Antibiotics, the Azalides"; The Journal Of Antibiotics, vol. XLI No. 8 pp. 1029–1047, 1988.

* cited by examiner

Primary Examiner—Elli Peselev
(74) Attorney, Agent, or Firm—Jason D. Ferrone

(57) ABSTRACT

The present invention discloses compounds of formula I, or pharmaceutically acceptable salts, esters, or prodrugs thereof:

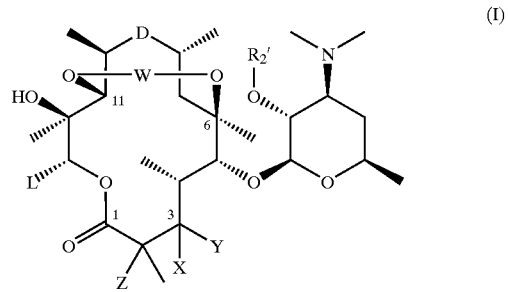

which exhibit antibacterial properties. The present invention further relates to pharmaceutical compositions comprising the aforementioned compounds for administration to a subject in need of antibiotic treatment. The invention also relates to methods of treating a bacterial infection in a subject by administering a pharmaceutical composition comprising the compounds of the present invention. The invention further includes process by which to make the compounds of the present invention.

8 Claims, No Drawings

6,11-4C-BICYCLIC 9A-AZALIDE DERIVATIVES

TECHNICAL FIELD

The present invention relates to novel semisynthetic macrolides having antibacterial activity and useful in the treatment and prevention of bacterial infections. More particularly, the invention relates to 6,11-4C-bicyclic 9a-azalide derivatives, compositions comprising such compounds, methods for using the same, and processes by which to make such compounds.

BACKGROUND OF THE INVENTION

Macrolide antibacterial agents are widely used to treat and prevent bacterial infections. However, the discovery of bacterial strains which have resistance or insufficient susceptibility to macrolide antibacterial agents has promoted the development of compounds with modified or improved profiles of antibiotic activity. One such class of compounds is azalides, which includes azithromycin, described in U.S. Pat. Nos. 4,474,768 and 4,517,359. Azalides are macrolide antibacterial agents with a ring structure similar to the erythronolide A or B, however azalides possess a substituted or unsubstituted nitrogen moiety at the 9a position as illustrated in the following structure:

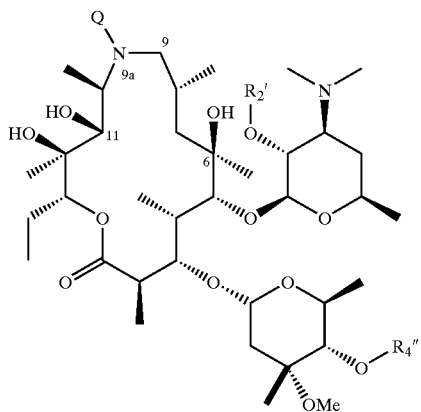

The potential for azalides to display modified or improved profiles for antibiotic activity has spawned extensive research to identify additional azalide derivatives with enhanced clinical properties. The following are examples of current efforts in azalide research:

PCT Application WO98/56801, published Dec. 17, 1998 discloses a series of 9a-(N-(alkyl))-azalide erythromycin A derivatives and a series of 9a-(N—(alkyl))-azalide 6-O-methylerythromycin A derivatives;

PCT Application WO98/56802, published Dec. 17, 1998 discloses a series of 9a-(N—(H))-azalide erythromycin A derivatives and a series of 9a-(N—(H))-azalide 6-O-methylerythromycin A derivatives;

PCT Application WO99/00124, published Jan. 7, 1999 discloses a series of 9a-(N—($R_n$))-azalide 3-thioxoerythromycin A derivatives and a series of 9a-(N—($R_n$))-azalide 6-O-methyl 3-oxoerythrmycin A derivatives, wherein $R_n$ is an optionally substituted alkyl or heteroalkyl;

PCT Application WO99/00125, published Jan. 7, 1999 discloses a series of 9a-(N—($R_n$))-azalide 3-oxoerythromycin A derivatives and a series of 9a-(N—($R_n$))-azalide 6-O-methyl 3-oxoerythromycin A derivatives, wherein $R_n$ is an optionally substituted alkyl or heteroalkyl; and U.S. Pat. No. 5,686,587 discloses a synthesis of azithromycin comprising introducing a 9a-(N(H))-moiety to erythromycin A by oxime formation, Beckmann rearrangement, reduction, and methylation.

SUMMARY OF THE INVENTION

The present invention provides a novel class of 6,11-4C-bicyclic 9a-azalide compounds, or a pharmaceutically-acceptable salt, ester, or prodrug thereof, pharmaceutical compositions comprising at least one compound of the present invention, methods of treating a bacterial infection in a subject by administering said pharmaceutical compositions, and processes of making the compounds of the present invention.

In one embodiment of the present invention there are disclosed compounds of formula I:

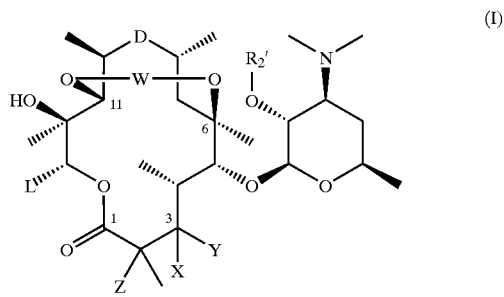

(I)

as well as the pharmaceutically acceptable salts, esters and prodrugs thereof, wherein:

W is
(a) —$CH_2$—C(A)=C(B)—$CH_2$—, wherein, A and B are independently selected from:
1. hydrogen;
2. deuterium;
3. halogen;
4. $R_1$, wherein $R_1$ is selected from:
   a. —$C_1$-$C_6$ alkyl, optionally substituted with one or more substituents selected from halogen, aryl, substituted aryl, heteroaryl, or substituted heteroaryl;
   b. —$C_2$-$C_6$ alkenyl, optionally substituted with one or more substituents selected from halogen, aryl, substituted aryl, heteroaryl, or substituted heteroaryl; or
   c. —$C_2$-$C_6$ alkynyl, optionally substituted with one or more substituents selected from halogen, aryl, substituted aryl, heteroaryl, or substituted heteroaryl;
5. $R_2$, wherein $R_2$ is selected from:
   a. aryl;
   b. heteroaryl;
   c. substituted aryl;
   d. substituted heteroaryl;
   e. heterocycloalkyl; or
   f. substituted heterocycloalkyl;
6. —($C_1$-$C_3$-alkyl)-M—($C_1$-$C_3$-alkyl)-$R_2$, wherein M=—O—, —NH—, —N($CH_3$)—, —NHC(O)— or —S(O)$_n$—, wherein n=0, 1 or 2, and $R_2$ is as previously defined;
7. —($C_1$-$C_3$-alkyl)-M—$R_2$, wherein M and $R_2$ are as previously defined;
8. —C(O)—V—$R_3$, wherein V is absent, O or S, and $R_3$ is H, $R_1$ or $R_2$; where $R_1$ and $R_2$ are as previously defined; or 9. —C(O)—NR$_{11}$R$_{12}$, wherein R$_1$ and R$_{12}$ are each independently selected from:
   a. hydrogen;
   b. —C$_1$–C$_6$-alkyl, optionally substituted with one or more substituents selected from halogen, aryl, substituted aryl, heteroaryl, or substituted heteroaryl;
   c. —C$_2$–C$_6$-alkenyl, optionally substituted with one or more substituents selected from halogen, aryl, substituted aryl, heteroaryl, or substituted heteroaryl;
   d. —C$_2$–C$_6$-alkynyl, optionally substituted with one or more substituents selected from halogen, aryl, substituted aryl, heteroaryl, or substituted heteroaryl; or
   in the alternative, R$_1$ and R$_{12}$ taken together with the nitrogen atom to which they are connected form a 3- to 7-membered ring which may optionally contain one or more double bonds and one or more heterofunctions selected from —O—, —NH—, —N(C$_1$–C$_6$-alkyl)—, —N(R$_2$)—, —S(O)$_n$—, wherein n and R$_2$ are as previously defined;

(b) —CH$_2$—CH(A)—C(B)=CH—, wherein A and B are as previously defined;

(c) —CH$_2$—CH(E)—CH(G)—CH$_2$—, wherein E and G are independently selected from
   1. A, wherein A is as previously defined;
   2. —OH;
   3. —OR$^p$, wherein R$^p$ is a hydroxy protecting group;
   4. —O—R$_9$, wherein R$_9$ is R$_1$ or R$_2$, and wherein R$_1$ and R$_2$ are as previously defined;
   5. —S(O)$_n$R$_9$, wherein n and R$_9$ are as previously defined;
   6. —NHC(O)R$_3$, wherein R$_3$ is as previously defined;
   7. —NHC(O)NR$_{11}$R$_3$, wherein R$_{11}$ and R$_3$ are as previously defined;
   8. —NHS(O)$_2$R$_9$, wherein R$_9$ is as previously defined;
   9. —NHR$_{13}$, wherein R$_{13}$ is an amino protecting group; or
   10. —NR$_{11}$R$_{12}$, wherein R$_{11}$ and R$_{12}$ are as previously defined;

(d)

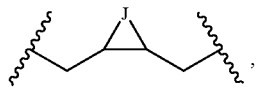

wherein —J— is selected from —O—; —O—C(O)—CH(R$_7$)—; —N(R$_7$)—; —O—C(O)—N(R$_7$)—; —O—C(O)—O—; —N(R$_7$)—N=N—; —C(R$_7$)=N—O—; or —CH(R$_7$)—N(R$_8$)—O—; wherein R$_7$ and R$_8$ are independently selected from R$_3$, wherein R$_3$ is as previously defined; or, in the alternative, —J— is taken with the two carbon atoms to which it is attached to form a cyclic moiety selected from
   a. C$_3$–C$_{12}$ cycloalkyl;
   b. C$_3$–C$_{12}$ cycloalkenyl; or
   c. heterocycloalkyl; or (e) —CH$_2$—C(R$_4$)(R$_5$)—CH$_2$CH$_2$—, wherein R$_4$ and R$_5$ taken together with the carbon atom to which they are attached are selected from:
   1. C=O;
   2. C(OR$_1$)$_2$, wherein R$_1$ is as previously defined;
   3. C(SR$_1$)$_2$, wherein R$_1$ is as previously defined;
   4. C(OR$_{12}$)(OR$_{13}$), where R$_{12}$ and R$_{13}$ taken together are —(CH$_2$)$_m$—, and where m is 2 or 3;
   5. C(SR$_{12}$)(SR$_{13}$), where R$_{12}$ and R$_{13}$ taken together are —(CH$_2$)$_m$—, where m is as previously defined;
   6. C=CHR$_3$, wherein R$_3$ is as previously defined;
   7. C=N—O—R$_3$, wherein R$_3$ is as previously defined;
   8. C=NNHR$_3$, wherein R$_3$ is as previously defined;
   9. C=NNHC(O)R$_3$, wherein R$_3$ is as previously defined;
   10. C=NNHC(O)NR$_{11}$R$_3$, wherein R$_{11}$ and R$_3$ are as previously defined;
   11. C=NNHS(O)$_2$R$_9$, wherein R$_9$ is as previously defined;
   12. C=NNHR$_{13}$, wherein R$_{13}$ is as previously defined; or
   13. C=NR$_9$, wherein R$_9$ is as previously defined;

L is
   (a) —CH$_3$;
   (b) —CH$_2$CH$_3$;
   (c) —CH(OH)CH$_3$;
   (d) —C$_1$–C$_6$ alkyl, optionally substituted with one or more substituents selected from aryl, substituted aryl, heteroaryl, or substituted heteroaryl;
   (e) C$_2$–C$_6$ alkenyl, optionally substituted with one or more substituents selected from aryl, substituted aryl, heteroaryl, or substituted heteroaryl; or
   (f) —C$_2$–C$_6$ alkynyl, optionally substituted with one or more substituents selected from aryl, substituted aryl, heteroaryl, or substituted heteroaryl;

D is —N(Q)CH$_2$—, —N(R')C(O)—, or —N=C(OR')—, wherein R' is R$_{11}$, as previously defined;

Q is
   (a) hydrogen;
   (b) —C$_1$–C$_{12}$-alkyl, C$_2$–C$_{12}$-alkenyl, or C$_2$–C$_{12}$-alkynyl, all optionally substituted with one, two or three substituents independently selected from:
   1. halogen;
   2. —OR$_6$, wherein R$_6$ is selected from:
      a. hydrogen;
      b. —C$_1$–C$_{12}$-alkyl containing 0, 1, 2, or 3 heteroatoms selected from O, S or N, optionally substituted with one, two, or three substituents independently selected from aryl, substituted aryl, heteroaryl, or substituted heteroaryl;
      c. aryl;
      d. substituted aryl;
      e. heteroaryl;
      f. substituted heteroaryl;
      g. heterocycloalkyl; or
      h. substituted heterocycloalkyl;
   3. —NR$_4$R$_5$, where R$_4$ and R$_5$ are each independently R$_6$, where R$_6$ is as previously defined, or in the alternative R$_4$ and R$_5$, together with the atom to which they are attached, form a heterocycloalkyl or substituted heterocycloalkyl moiety;
   4. =N—O—R$_6$, where R$_6$ is as previously defined;
   5. —R$_1$, where R$_1$ is as previously defined;
   6. —C$_3$–C$_{12}$-cycloalkyl;
   7. substituted —C$_3$–C$_{12}$cycloalkyl;
   8. heterocycloalkyl;
   9. substituted heterocycloalkyl;
   10. —NHC(O)R$_6$, where R$_6$ is as previously defined;
   11. —NHC(O)OR$_7$, where R$_7$ is selected from:
      a. C$_1$–C$_{12}$-alkyl containing 0, 1, 2, or 3 heteroatoms selected from O, S or N, optionally substituted with one, two, or three substituents independently selected from aryl, substituted aryl, heteroaryl, or substituted heteroaryl;
b. aryl;
c. substituted aryl;
d. heteroaryl;
e. substituted heteroaryl;
f. heterocycloalkyl; or
g. substituted heterocycloalkyl;
12. —NHC(O)NR$_4$R$_5$, where R$_4$ and R$_5$ are as previously defined;
13. —OC(O)NR$_4$R$_5$, where R$_4$ and R$_5$ are as previously defined;
14. —OC(O)R$_7$, where R$_7$ is as previously defined;
15. —OC(O)OR$_7$, where R$_7$ is as previously defined;
16. —OC(O)NR$_4$R$_5$, where R$_4$ and R$_5$ are as previously defined,
17. —C(O)R$_6$, where R$_6$ is as previously defined,
18. —CO$_2$R$_6$, where R$_6$ is as previously defined, or
19. —C(O)NR$_4$R$_5$, where R$_4$ and R$_5$ are as previously defined;

X is hydrogen;
Y is
(a) hydrogen;
(b) —OH;
(c) —OR$_p$, where R$_p$ is as previously defined;
(d) —OR$_y$, where R$_y$ is R$_1$ and R$_2$ as previously defined;
(e) —OC(O)R$_y$, where R$_y$ is R$_1$ and R$_2$ as previously defined;
(f) —OC(O)NHR$_y$, where R$_y$ is R$_1$ and R$_2$ as previously defined;
(g) —S(O)$_n$R$_y$, where n is previously defined and R$_y$ is R$_1$ and R$_2$ as previously defined;

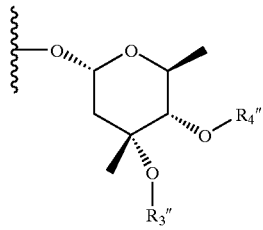

where R$_3$" is hydrogen or methyl; R$_4$" is hydrogen or R$_p$, where R$_p$ is as previously defined; or
(h) in the alternative, X and Y combined together are oxo;

Z is
(a) hydrogen;
(b) methyl; or
(c) halogen; and

R$_2$' is hydrogen or R$_p$, where R$_p$ is as previously defined.

In another embodiment of the present invention there are disclosed pharmaceutical compositions comprising a therapeutically effective amount of a compound of the invention in combination with a pharmaceutically acceptable carrier or excipient. In yet another embodiment of the invention are methods of treating antibacterial infections with said pharmaceutical compositions. Suitable carriers and methods of formulation are also disclosed.

In a further aspect of the present invention there are provided processes for the preparation of 6,11-4C-bicyclic 9a-azalide derivatives of formula (I).

DETAILED DESCRIPTION OF THE INVENTION

A first embodiment of the present invention is a compound of formula I as illustrated above, or a pharmaceutically acceptable salt, ester or prodrug thereof.

Preferred subgenera of compounds of the present invention are:

A compound of the formula II:

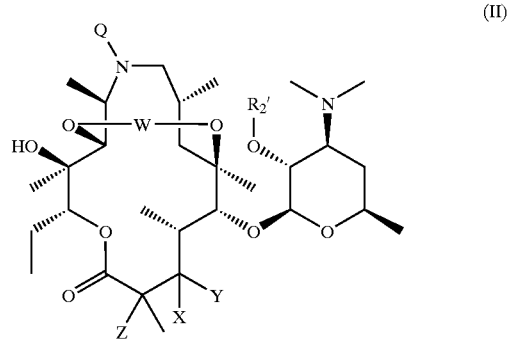

(II)

wherein Q, W, X, Y, Z and R$_2$' are as previously defined;

A compound of formula III:

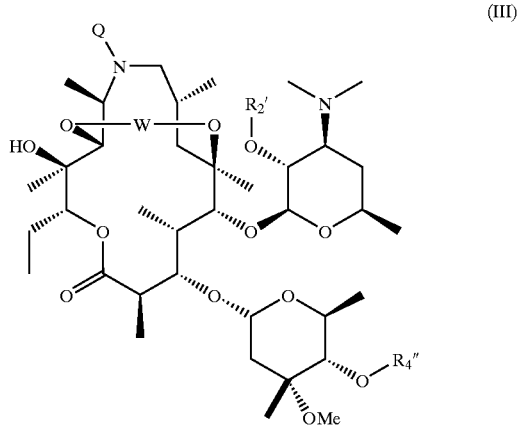

(III)

wherein W, Q, R$_2$', and R$_4$" are as previously defined;
compound of formula IV:

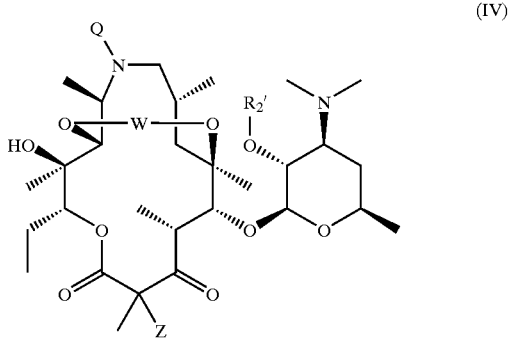

(IV)

wherein W, O, Z and R$_2$' are as previously defined;

A compound of formula V:

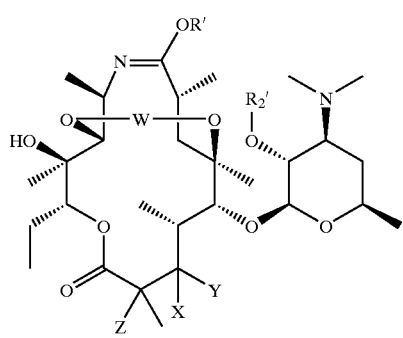
(V)

wherein W, X, Y, Z, R', and R₂' are as previously defined;

A compound of formula VI:

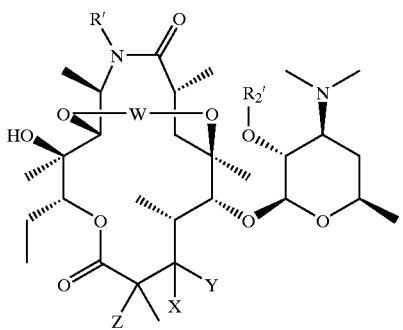
(VI)

wherein W, X, Y, R', and R₂' are as previously defined;

A compound of formula VII:

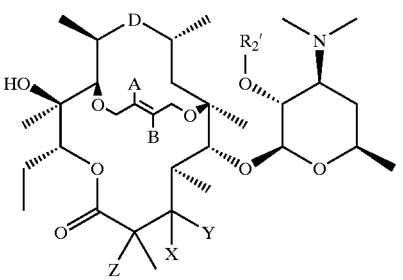
(VII)

wherein A, B, D, X, Y, Z, and R₂¹' are as previously defined;

A compound of formula VIII:

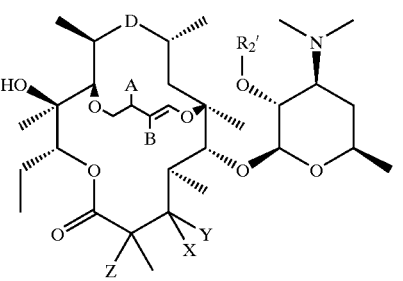
(VIII)

wherein A, B, D, X, Y, Z, and R₂' are as previously defined;

A compound of formula IX:

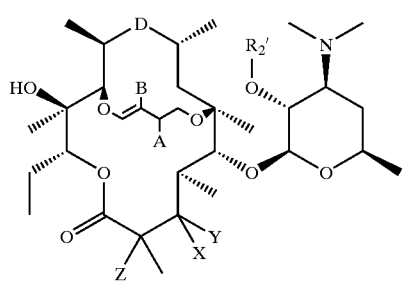
(IX)

wherein A, B, D, X, Y, Z, and R₂' are as previously defined;

A compound of formula X:

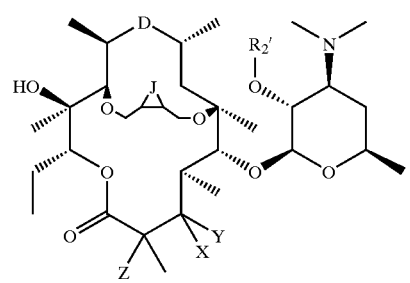
(X)

wherein D, J, X, Y, Z, and R₂' are as previously defined; or

A compound of formula XI:

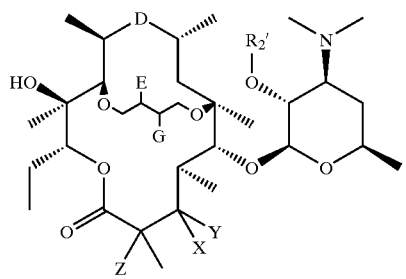
(XI)

wherein D, E, G, X, Y, Z, and R₂' are as previously defined.

Representative compounds according to the invention are those selected from:

Compound of formula I, wherein W is —CH₂CH=CHCH₂—, D=—N=CH(OMe)—, X=Z=H,

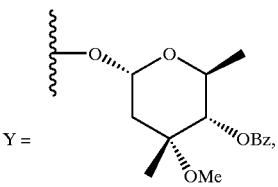

Y =

L=CH$_2$CH$_3$, and R$_2$'=Bz;
Compound of formula I, wherein W is —CH$_2$CH=CHCH$_2$—, D=—NHCH$_2$—, X=Z=H, Y = 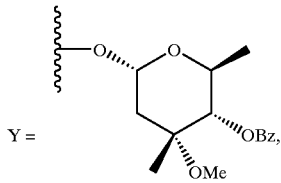

L=CH$_2$CH$_3$, and R$_2$'=Bz;
Compound of formula I, wherein W is —CH$_2$CH=CHCH$_2$—, D=—NHCH$_2$, X=Z=H, Y = 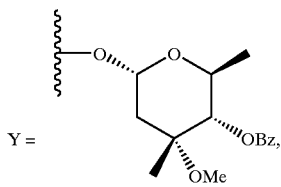

L=CH$_2$CH$_3$, and R$_2$'=H;
Compound of formula I, wherein W is —CH$_2$CH=CHCH$_2$—, D=—NHCH$_2$—, X=Z=H, Y=OH, L=CH$_2$CH$_3$, and R$_2$'=H;
Compound of formula I, wherein W is —CH$_2$CH=CHCH$_2$—, D=—NHCH$_2$—, X and Y are taken together with the carbon to which they are attached are C=O, L=CH$_2$CH$_3$, and R$_2$'=H;
A compound of formula I, wherein W is —CH$_2$CH=CHCH$_2$—, D=—NHC(O)—, X=Z=H, L=—CH$_2$CH$_3$, Y = 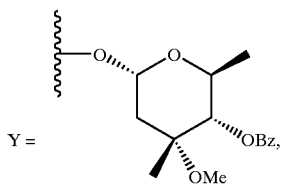

R$_2$'=H;
A compound of formula I, wherein W is —CH$_2$CH=CHCH$_2$—, D=—N(Q)CH$_2$—, Q=CH$_3$, X=Z=H, Y=OH, L=CH$_2$CH$_3$, R$_2$'=H;
A compound of formula I, wherein W is —CH$_2$CH=CHCH$_2$—, D=—N(Q)CH$_2$—, Q=CH$_3$, Z=H, X and Y taken together are oxo, L=CH$_2$CH$_3$, R$_2$'=H;
A compound of formula I, wherein W is —CH$_2$CH=CHCH$_2$—, D=—N(Q)CH$_2$—, Q=CH$_2$Ph, Z=X=H, Y=OH, L=CH$_2$CH$_3$, R$_2$'=H;
A compound of formula I, wherein W is —CH$_2$CH=CHCH$_2$—, D=—N(Q)CH$_2$—, Q=CH$_2$Ph, Z=H, X and Y are taken together are oxo, L=CH$_2$CH$_3$, R$_2$'=H;
A compound of formula I, wherein W is —CH$_2$CH=CHCH$_2$—, D=—N(Q)CH$_2$—, Q=CH$_2$(2-pyridyl), Z=X=H, Y=OH, L=CH$_2$CH$_3$, R$_2$'=H;
A compound of formula I, W is —CH$_2$CH=CHCH$_2$—, D=—N(Q)CH, Q=CH$_2$(2-pyridyl), Z=H, X and Y taken together are oxo, L=CH$_2$CH$_3$, R$_2$'=H;
A compound of formula I, wherein W is —CH$_2$CH=CHCH$_2$—, D=—N(Q)CH$_2$—, Q=CH$_2$(3-quinolyl), Z=H, X and Y taken together are oxo, L=CH$_2$CH$_3$, R$_2$'=H;
A compound of formula I, wherein W is —CH$_2$CH=CHCH$_2$—, D=—N(Q)CH$_2$—, Q=CH$_2$(3-quinolyl), Z=H, X and Y taken together are oxo, L=CH$_2$CH$_3$, R$_2$'=H;
A compound of formula I, wherein W is —CH$_2$CH=CHCH$_2$—, D=—N(Q)CH$_2$—, Q=CH$_2$(CH=CH)Ph, Z=X=H, Y=OH, L=CH$_2$CH$_3$, R$_2$'=H;
A compound of formula I, wherein W is —CH$_2$CH=CHCH$_2$—, D=—N(Q)CH$_2$—, Q=CH$_2$(CH=CH)Ph, Z=H, X and Y taken together are oxo, L=CH$_2$CH$_3$, R$_2$'=H;
A compound of formula I, wherein W is —CH$_2$CH=CHCH$_2$—, D=—N(Q)CH$_2$—, Q=CH$_2$CH=CH(2-pyridyl), Z=X=H, Y=OH, L=CH$_2$CH$_3$, R$_2$'=H;
A compound of formula I, wherein A and B taken together with the carbon atom to which they are attached=C=CH$_2$, D=—N(Q)CH$_2$—, Q=CH$_2$CH=CH(2-pyridyl), Z=H, X and Y taken together are oxo, L=CH$_2$CH$_3$, R$_2$'=H;
A compound of formula I, wherein W is —CH$_2$CH=CHCH$_2$—, D=—N(Q)CH$_2$—, Q=CH$_2$C≡C(3-quinolyl), Z=X=H, Y=OH, L=CH$_2$CH$_3$, R$_2$'=H; or
A compound of formula I, wherein W=—CH$_2$CH=CHCH$_2$—, D=—N(Q)CH$_2$—, Q=CH$_2$C≡C(3-quinolyl), Z=H, X and Y taken together are oxo, L=CH$_2$CH$_3$, R$_2$'=H.

A further embodiment of the present invention includes pharmaceutical compositions comprising any single compound delineated herein, or a pharmaceutically acceptable salt, ester, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, or prodrug thereof, with a pharmaceutically acceptable carrier or excipient.

Yet a further embodiment of the present invention is a pharmaceutical composition comprising any single compound delineated herein in combination with one or more antibiotics known in the art, or a pharmaceutically acceptable salt, ester, or prodrug thereof, with a pharmaceutically acceptable carrier or excipient.

In addition, the present invention contemplates processes of making any compound delineated herein via any synthetic method delineated herein.

Definitions

Listed below are definitions of various terms used to describe this invention. These definitions apply to the terms as they are used throughout this specification and claims, unless otherwise limited in specific instances, either individually or as part of a larger group.

The terms "$C_1$–$C_3$ alkyl," "$C_1$–$C_6$ alkyl," or "$C_1$–$C_{12}$ alkyl," as used herein, refer to saturated, straight- or branched-chain hydrocarbon radicals containing between one and three, one and twelve, or one and six carbon atoms, respectively. Examples of $C_1$–$C_3$ alkyl radicals include methyl, ethyl, propyl and isopropyl radicals; examples of $C_1$–$C_6$ alkyl radicals include, but are not limited to, methyl, ethyl, propyl, isopropyl, n-butyl, tert-butyl, neopentyl and n-hexyl radicals; and examples of $C_1$–$C_{12}$ alkyl radicals include, but are not limited to, ethyl, propyl, isopropyl, n-hexyl, octyl, decyl, dodecyl radicals.

The term "substituted alkyl," as used herein, refers to a "$C_2$–$C_{12}$ alkyl" or "$C_1$–$C_6$ alkyl" group as previously defined, substituted by independent replacement or one, two, or three of the hydrogen atoms thereon with substituents including, but not limited to, —F, —Cl, —Br, —I, —OH, protected hydroxy, —$NO_2$, —CN, —$C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$-$C_{12}$-alkenyl, —O—$C_2$–$C_{12}$-alkenyl, —O—$C_3$–$C_{12}$-cycloalkyl, —O-aryl, —O-heteroaroyl, —O-heterocycloalkyl, —C(O)—$C_1$–$C_{12}$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkenyl, —$OCO_2$—$C_3$–$C_{12}$-cycloalkyl, —$OCO_2$—aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkenyl, —$NHCO_2$—$C_3$–$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O) NH-aryl, —NHC(O)NH-heteroaryl, —NHC(O)NH-heterocycloalkyl, NHC(S)$NH_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —NHC(NH)$NH_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_{1-C12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)—heteroaryl, —S(O)-heterocycloalkyl —$SO_2NH_2$, —$SO_2NH$—$C_1$–$C_{12}$-alkyl, —$SO_2NH$—$C_2$–$C_{12}$-alkenyl, —$SO_2NH$—$C_2$–$C_{12}$-alkenyl, —$SO_2NH$—$C_3$–$C_{12}$-cycloalkyl, —$SO_2NH$-aryl, —$SO_2NH$-heteroaryl, —$SO_2NH$-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The terms "$C_2$–$C_{12}$ alkenyl" or "$C_2$–$C_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, and the like.

The term "substituted alkenyl," as used herein, refers to a "$C_2$–$C_2$ alkenyl" or "$C_2$–$C_6$ alkenyl" group as previously defined, substituted by independent replacement or one, two, or three of the hydrogen atoms thereon with substituents including, but not limited to, —F, —Cl, —Br, —I, —OH, protected hydroxy, —$NO_2$, —CN, —$C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—-$C_2$–$C_{12}$-alkenyl, —O—-$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkenyl, —$OCO_2$—$C_3$–$C_{12}$-Cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkenyl, —$NHCO_2$—$C_3$–$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, NHC(S) $NH_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —NHC(NH)$NH_2$, NHC(NH)NH—$C_1$–$C_{12}$-alkyl, —NHC(NH)$NHC_2$—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_2$-alkyl, —NHC(NH)—$C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$- alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkenyl, —$SO_2NH$—$C_3$-$C_{12}$-cycloalkyl, —$SO_2NH$-aryl, —$SO_2NH$-heteroaryl, $SO_2NH$-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$-$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

The terms "$C_2$-$C_{12}$ alkynyl" or "$C_2$-$C_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "$C_2$-$C_{12}$ alkynyl" or "$C_2$-$C_6$ alkynyl" group as previously defined, substituted by independent replacement or one, two, or three of the hydrogen atoms thereon with substituents including, but not limited to, —F, —Cl, —Br, —I, —OH, protected hydroxy, —$NO_2$, —CN, —$C_1$-$C_{12}$-alkyl optionally substituted with halogen, $C_2$-$C_{12}$-alkenyl optionally substituted with halogen, —$C_2$-$C_{12}$-alkynyl optionally substituted with halogen, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$, -aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$—$C_{12}$-cycloalkyl, —S(O)-aryl, —S(O)-heteroaryl, —S(O)-heterocycloalkyl —$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkenyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

The term "$C_1$-$C_6$ alkoxy," as used herein, refers to a $C_1$-$C_6$ alkyl group, as previously defined, attached to the parent molecular moiety through an oxygen atom. Examples of $C_1$-$C_6$-alkoxy include, but are not limited to, methoxy, ethoxy, propoxy, isopropoxy, n-butoxy, tert-butoxy, neopentoxy and n-hexoxy.

The terms "halo" and "halogen," as used herein, refer to an atom selected from fluorine, chlorine, bromine and iodine.

The term "aryl," as used herein, refers to a mono- or bicyclic carbocyclic ring system having one or two aromatic rings including, but not limited to, phenyl, naphthyl, tetrahydronaphthyl, indanyl, idenyl and the like.

The term "substituted aryl," as used herein, refers to an aryl group, as previously defined, substituted by independent replacement or one, two, or three of the hydrogen atoms thereon with substituents including, but not limited to, —F, —Cl, —Br, —I, —OH, protected hydroxy, —$NO_2$, —CN, —$C_1$-$C_{12}$-alkyl optionally substituted with halogen, $C_2$-$C_{12}$-alkenyl optionally substituted with halogen, —$C_2$-$C_{12}$-alkynyl optionally substituted with halogen, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—

$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, –NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkenyl, —$NHCO_2$—$C_3$–$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, NHC(S)$NH_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —NHC(NH)$NH_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl —$SO_2NH_2$, —$SO_2$NH—$C_1$–$C_{12}$-alkyl, —$SO_2$NH—$C_2$–$C_{12}$-alkenyl, —$SO_2$NH—$C_2$–$C_{12}$-alkenyl, —$SO_2$NH—$C_3$–$C_{12}$-cycloalkyl, —$SO_2$NH-aryl, —$SO_2$NH-heteroaryl, —$SO_2$NH-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The term "arylalkyl," as used herein, refers to a $C_1$–$C_3$ alkyl or $C_1$–$C_6$ alkyl residue attached to an aryl ring. Examples include, but are not limited to, benzyl, phenethyl and the like.

The term "substituted arylalkyl," as used herein, refers to an arylalkyl group, as previously defined, substituted by independent replacement or one, two, or three of the hydrogen atoms thereon with substituents including, but not limited to, but not limited to, —F, —Cl, —Br, —I, —OH, protected hydroxy, —$NO_2$, —CN, —$C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkenyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkenyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkenyl, —$NHCO_2$—$C_3$–$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, NHC(S)$NH_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —NHC(NH)$NH_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl-$SO_2NH_2$, —$SO_2$NH—$C_1$–$C_{12}$-alkyl, —$SO_2$NH—$C_2$–$C_{12}$-alkenyl, —$SO_2$NH—$C_2$–$C_{12}$-alkenyl, —$SO_2$NH—$C_3$–$C_{12}$-cycloalkyl, —$SO_2$NH-aryl, —$SO_2$NH-heteroaryl, —$SO_2$NH-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The term "heteroaryl," as used herein, refers to a mono-, bi-, or tri-cyclic aromatic radical or ring having from five to ten ring atoms of which one ring atom is selected from S, O and N; zero, one or two ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "substituted heteroaryl," as used herein, refers to a heteroaryl group as previously defined, substituted by independent replacement or one, two, or three of the hydrogen atoms thereon with substituents including, but not limited to, —F, —Cl, —Br, —I, —OH, protected hydroxy, —NO$_2$, —CN, —C$_1$–C$_{12}$-alkyl optionally substituted with halogen, C$_2$–C$_{12}$-alkenyl optionally substituted with halogen, —C$_2$–C$_{12}$-alkynyl optionally substituted with halogen, —NH$_2$, protected amino, —NH—C$_1$–C$_{12}$-alkyl, —NH—C$_2$–C$_{12}$-alkenyl, —NH—C$_2$–C$_{12}$-alkenyl, —NH—C$_3$–C$_{12}$-cycloalkyl, —NH-aryl, —NH-heteroaryl, —NH-heterocycloalkyl, -dialkylamino, -diarylamino, -diheteroarylamino, —O—C$_1$–C$_{12}$-alkyl, —O—C$_2$–C$_{12}$-alkenyl, —O—C$_2$–C$_{12}$-alkenyl, —O—C$_3$–C$_{12}$-cycloalkyl, —O-aryl, —O-heteroaryl, —O-heterocycloalkyl, —C(O)—C$_1$–C$_{12}$-alkyl, —C(O)—C$_2$–C$_{12}$-alkenyl, —C(O)—C$_2$–C$_{12}$-alkenyl, —C(O)—C$_3$–C$_{12}$-cycloalkyl, —C(O)-aryl, —C(O)-heteroaryl, —C(O)-heterocycloalkyl, —CONH$_2$, —CONH—C$_1$–C$_{12}$-alkyl, —CONH—C$_2$–C$_{12}$-alkenyl, —CONH—C$_2$–C$_{12}$-alkenyl, —CONH—C$_3$–C$_{12}$-cycloalkyl, —CONH-aryl, —CONH-heteroaryl, —CONH-heterocycloalkyl, —OCO$_2$—C$_1$–C$_{12}$-alkyl, —OCO$_2$—C$_2$–C$_{12}$-alkenyl, —OCO$_2$—C$_2$–C$_{12}$-alkenyl, —OCO$_2$—C$_3$–C$_{12}$-cycloalkyl, —OCO$_2$-aryl, —OCO$_2$-heteroaryl, —OCO$_2$-heterocycloalkyl, —OCONH$_2$, —OCONH—C$_1$–C$_{12}$-alkyl, —OCONH—C$_2$–C$_{12}$-alkenyl, —OCONH—C$_2$–C$_{12}$-alkenyl, —OCONH—C$_3$–C$_{12}$-cycloalkyl, —OCONH-aryl, —OCONH-heteroaryl, —OCONH-heterocycloalkyl, —NHC(O)—C$_1$–C$_{12}$-alkyl, —NHC(O)—C$_2$–C$_{12}$-alkenyl, —NHC(O)—C$_2$–C$_{12}$-alkenyl, —NHC(O)—C$_3$–C$_{12}$-cycloalkyl, —NHC(O)-aryl, —NHC(O)-heteroaryl, —NHC(O)-heterocycloalkyl, —NHCO$_2$—C$_1$–C$_{12}$-alkyl, —NHCO$_2$—C$_2$–C$_{12}$-alkenyl, —NHCO$_2$—C$_2$–C$_{12}$-alkenyl, —NHCO$_2$—C$_3$–C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$–C$_{12}$-alkyl, —NHC(O)NH—C$_2$–C$_{12}$-alkenyl, —NHC(O)NH—C$_2$–C$_{12}$-alkenyl, —NHC(O)NH—C$_3$–C$_2$-cycloalkyl, —NHC(O)NH-aryl, —NHC(O)NH-heteroaryl, —NHC(O)NH-heterocycloalkyl, NHC(S)NH$_2$, NHC(S)NH—C$_1$–C$_{12}$-alkyl, —NHC(S)NH—C$_2$–C$_2$-alkenyl, —NHC(S)NH—C$_2$–C$_{12}$-alkenyl, —NHC(S)NH—C$_3$–C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$–C$_{12}$-alkyl, —NHC(NH)NH—C$_2$–C$_{12}$-alkenyl, —NHC(NH)NH—C$_2$–C$_{12}$-alkenyl, —NHC(NH)NH—C$_3$–C$_{12}$-cycloalkyl, —NHC(NH)NH-aryl, —NHC(NH)NH-heteroaryl, —NHC(NH)NH-heterocycloalkyl, NHC(NH)—C$_1$–C$_{12}$-alkyl, —NHC(NH)—C$_2$–C$_{12}$-alkenyl, —NHC(NH)—C$_2$–C$_{12}$-alkenyl, —NHC(NH)—C$_3$–C$_{12}$-cycloalkyl, —NHC(NH)-aryl, —NHC(NH)-heteroaryl, —NHC(NH)-heterocycloalkyl, —C(NH)NH—C$_1$–C$_{12}$-alkyl, —C(NH)NH—C$_2$–C$_{12}$-alkenyl, —C(NH)NH—C$_2$–C$_{12}$-alkenyl, —C(NH)NH—C$_3$–C$_{12}$-cycloalkyl, —C(NH)NH-aryl, —C(NH)NH-heteroaryl, —C(NH)NH-heterocycloalkyl, —S(O)—C$_1$–C$_{12}$-alkyl, —S(O)—C$_2$–C$_{12}$-alkenyl, —S(O)—C$_2$–C$_{12}$-alkenyl, —S(O)—C$_3$–C$_{12}$cycloalkyl, —S(O)-aryl, —S(O)-heteroaryl, —S(O)-heterocycloalkyl-SO$_2$NH$_2$, —SO$_2$NH—C$_1$–C$_{12}$-alkyl, —SO$_2$NH—C$_2$–C$_{12}$-alkenyl, —SO$_2$NH—C$_2$–C$_{12}$-alkenyl, —SO$_2$NH—C$_3$–C$_{12}$-cycloalkyl, —SO$_2$NH-aryl, —SO$_2$NH-heteroaryl, —SO$_2$NH-heterocycloalkyl, —NHSO$_2$—C$_1$–C$_{12}$-alkyl, —NHSO$_2$—C$_2$–C$_{12}$-alkenyl, —NHSO$_2$—C$_2$–C$_{12}$-alkenyl, —NHSO$_2$—C$_3$–C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$–C$_{12}$-cycloalkyl, -methoxymethoxy, -methoxyethoxy, —SH, —S—C$_1$–C$_{12}$-alkyl, —S—C$_2$–C$_{12}$-alkenyl, —S—C$_2$–C$_{12}$-alkenyl, —S—C$_3$–C$_{12}$-cycloalkyl, —S-aryl, —S-heteroaryl, —S-heterocycloalkyl, or methylthiomethyl.

The term "C$_3$–C$_{12}$-cycloalkyl," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1] heptyl, and bicyclo[2.2.2] octyl.

The term "substituted C$_3$–C$_{12}$-cycloalkyl," as used herein, refers to a C$_3$–C$_{12}$-cycloalkyl group as previously defined, substituted by independent replacement or one, two, or three of the hydrogen atoms thereon with substituents including, but not limited to, —F, —Cl, —Br, —I, —OH, protected hydroxy, —NO$_2$, —CN, —C$_1$–C$_{12}$-alkyl optionally substituted with halogen, C$_2$–C$_{12}$-alkenyl optionally substituted with halogen, —C$_2$–C$_{12}$-alkynyl optionally substituted with halogen, —NH$_2$, protected amino, —NH—C$_1$–C$_{12}$-alkyl, —NH—C$_2$–C$_{12}$-alkenyl, —NH—C$_2$–C$_{12}$-alkenyl, —NH—C$_3$–C$_{12}$-cycloalkyl, —NH-aryl, —NH-heteroaryl, —NH-heterocycloalkyl, -dialkylamino, -diarylamino, -diheteroarylamino, —O—C$_1$–C$_{12}$-alkyl, —O—C$_2$–C$_{12}$-alkenyl, —O—C$_2$–C$_{12}$-alkenyl, —O—C$_3$–C$_{12}$-cycloalkyl, —O-aryl, —O-heteroaryl, —O-heterocycloalkyl, —C(O)—C$_1$–C$_{12}$-alkyl, —C(O)—C$_2$–C$_{12}$-alkenyl, —C(O)—C$_2$–C$_{12}$-alkenyl, —C(O)—C$_3$–C$_{12}$-cycloalkyl, —C(O)-aryl, —C(O)-heteroaryl, —C(O)-heterocycloalkyl, —CONH$_2$, —CONH—C$_1$–C$_{12}$-alkyl, —CONH—C$_2$–C$_{12}$-alkenyl, —CONH—C$_2$–C$_{12}$-alkenyl, —CONH—C$_3$–C$_{12}$-cycloalkyl, —CONH-aryl, —CONH-heteroaryl, —CONH-heterocycloalkyl, —OCO$_2$—C$_1$–C$_{12}$-alkyl, —OCO$_2$—C$_2$–C$_{12}$-alkenyl, —OCO$_2$—C$_3$–C$_{12}$-cycloalkyl, —OCO$_2$—C$_3$–C$_{12}$-cycloalkyl, aryl, —OCO$_2$-heteroaryl, —OCO$_2$-heterocycloalkyl, —OCONH$_2$, —OCONH—C$_1$–C$_{12}$-alkyl, —OCONH—C$_2$–C$_{12}$-alkenyl, —OCONH—C$_2$–C$_{12}$-alkenyl, —OCONH—C$_3$–C$_{12}$-cycloalkyl, —OCONH-aryl, —OCONH-heteroaryl, —OCONH-heterocycloalkyl, —NHC(O)—C$_1$–C$_{12}$-alkyl, —NHC(O)—C$_2$–C$_{12}$-alkenyl, —NHC(O)—C$_2$–C$_{12}$-alkenyl, —NHC(O)—C$_3$–C$_{12}$-cycloalkyl, —NHC(O)-aryl, —NHC(O)-heteroaryl, —NHC(O)-heterocycloalkyl, —NHCO$_2$—C$_1$–C$_{12}$-alkyl, —NHCO$_2$—C$_2$–C$_{12}$-alkenyl, —NHCO$_2$—C$_2$–C$_{12}$-alkenyl, —NHCO$_2$—C$_3$–C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$–C$_{12}$-alkyl, —NHC(O)NH—C$_2$–C$_{12}$-alkenyl, —NHC(O)NH—C$_2$–C$_{12}$-alkenyl, —NHC(O)NH—C$_3$–C$_{12}$-cycloalkyl, —NHC(O) NH-aryl, —NHC(O)NH-heteroaryl, —NHC(O)NH-heterocycloalkyl, NHC(S)NH$_2$, NHC(S)NH—C$_1$–C$_{12}$-alkyl, —NHC(S)NH—C$_2$–C$_{12}$-alkenyl, —NHC(S)NH—C$_2$–C$_{12}$-alkenyl, —NHC(S)NH—C$_3$–C$_{12}$-cycloalkyl, —NHC(S) NH-aryl, —NHC(S)NH-heteroaryl, —NHC(S)NH-heterocycloalkyl, —NHC(NH)NH$_2$, NHC(NH)NH—C$_1$–C$_{12}$-alkyl, —NHC(NH)NH—C$_2$–C$_{12}$-alkenyl, —NHC(NH)NH—C$_1$–C$_{12}$-alkenyl, —NHC(NH)NH—C$_3$–C$_{12}$-cycloalkyl, —NHC(NH)NH-aryl, —NHC(NH)NH-heteroaryl, —NHC(NH)NH-heterocycloalkyl, NHC(NH)—C$_1$–C$_{12}$-alkyl, —NHC(NH)—C$_2$–C$_{12}$-alkenyl, —NHC(NH)—C$_2$–C$_{12}$-alkenyl, —NHC(NH)—C$_3$–C$_{12}$-cycloalkyl, —NHC(NH)-aryl, —NHC(NH)-heteroaryl, —NHC(NH)-heterocycloalkyl, —C(NH)NH—C$_1$–C$_{12}$-alkyl, —C(NH)NH—C$_2$–C$_{12}$-alkenyl, —C(NH)NH—C$_2$–C$_{12}$-alkenyl, —C(NH)NH—C$_3$–C$_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl —$SO_2NH_2$, —$SO_2NH$—$C_1$–$C_{12}$-alkyl, —$SO_2NH$—$C_2$–$C_{12}$-alkenyl, —$SO_2NH$—$C_2$–$C_{12}$-alkenyl, —$SO_2NH$—$C_3$–$C_{12}$-cycloalkyl, —$SO_2NH$-aryl, —$SO_2NH$-heteroaryl, —$SO_2NH$-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The term "$C_3$–$C_{12}$-cycloalkenyl," as used herein, denotes a monocyclic or bicyclic carbocyclic ring compound where each 5-membered ring has 0 to 1 double bonds and each 6-membered ring has 0 to 2 double bonds. Examples include, but not limited to, cyclopentenyl, cyclohexenyl, bicyclo[2.2.1] heptenyl, and bicyclo[2.2.2] octenyl.

The term "heterocycloalkyl," as used herein, refers to a non-aromatic 5-, 6-or 7-membered ring or a bi-or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted heterocycloalkyl," as used herein, refers to a heterocycloalkyl group, as previously defined, substituted by independent replacement or one, two, or three of the hydrogen atoms thereon with substituents including, but not limited to, —F, —Cl, —Br, —I, —OH, protected hydroxy, —$NO_2$, —CN, —$C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkenyl, —O—$C_3$–$C_{12}$-cycloalkyl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkenyl, —CON H—$C_3$–$C_{12}$-cycloalkyl, —CONH-aryl, CONH-heteroaryl, —CONH-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkenyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$clycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkenyl, —$NHCO_2$—$C_3$–$C_{12}$-cycloalkyl, —$NHCO_2$-aryl, —$NHCO_2$-heteroaryl, —$NHCO_2$-heterocycloalkyl, —$NHC(O)NH_2$, NHC(O)NH—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, $NHC(S)NH_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —$NHC(NH)NH_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl —$SO_2NH_2$, —$SO_2NH$—$C_1$–$C_{12}$-alkyl, —$SO_2NH$—$C_2$–$C_{12}$-alkenyl, —$SO_2NH$—$C_2$–$C_{12}$-alkenyl, —$SO_2NH$—$C_3$–$C_{12}$-cycloalkyl, —$SO_2NH$-aryl, —$SO_2NH$-heteroaryl, —$SO_2NH$-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The term "heteroarylalkyl," as used herein, refers to a $C_1$–$C_3$ alkyl or $C_1$–$C_6$ alkyl residue residue attached to a heteroaryl ring. Examples include, but are not limited to, pyridinylmethyl, pyrimidinylethyl and the like.

The term "substituted heteroarylalkyl," as used herein, refers to a heteroarylalkyl group, as previously defined, substituted by independent replacement or one, two, or three of the hydrogen atoms thereon with substituents including, but not limited to, —F, —Cl, —Br, —I, —OH, protected hydroxy, —$NO_2$, —CN, $C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkenyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkenyl, —CONH —$C_3$–$C_{12}$-cycloalkyl, —CONH-aryl, —CONH-heteroaryl, —CONH-heterocycloalkyl, —OCO$_2$—C$_1$–C$_{12}$-alkyl, —OCO$_2$—C$_2$–C$_{12}$-alkenyl, —OCO$_2$—C$_2$–C$_{12}$-alkenyl, —OCO$_2$—C$_3$–C$_{12}$-cycloalkyl, —OCO$_2$-aryl, —OCO$_2$-heteroaryl, —OCO$_2$-heterocycloalkyl, —OCONH$_2$, —OCONH—C$_1$–C$_{12}$-alkyl, —OCONH—C$_2$–C$_2$-alkenyl, —OCONH—C$_2$–C$_2$-alkenyl, —OCONH—C$_3$–C$_{12}$-cycloalkyl, —OCONH-aryl, —OCONH-heteroaryl, —OCONH-heterocycloalkyl, —NHC(O)—C$_1$–C$_{12}$-alkyl, —NHC(O)—C$_2$–C$_{12}$-alkenyl, —NHC(O)—C$_2$–C$_{12}$-alkenyl, —NHC(O)—C$_3$–C$_{12}$-cycloalkyl, —NHC(O)-aryl, —NHC(O)-heteroaryl, —NHC(O)-heterocycloalkyl, —NHCO$_2$—C$_1$–C$_{12}$-alkyl, —NHCO$_2$—C$_2$–C$_{12}$-alkenyl, —NHCO$_2$—C$_2$–C$_{12}$-alkenyl, —NHCO$_2$—C$_3$–C$_{12}$-cycloalkyl, —NHCO$_2$-aryl, NHCO$_2$-heteroaryl, —NHCO$_2$-heterocycloalkyl, —NHC(O)NH$_2$, NHC(O)NH—C$_1$–C$_{12}$-alkyl, —NHC(O)NH—C$_2$–C$_{12}$-alkenyl, —NHC(O)NH—C$_2$–C$_{12}$-alkenyl, —NHC(O)NH—C$_3$–C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$–C$_{12}$-alkyl, —NHC(S)NH—C$_2$–C$_{12}$-alkenyl, —NHC(S)NH—C$_2$–C$_{12}$-alkenyl, —NHC(S)NH—C$_3$–C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$–C$_{12}$-alkyl, —NHC(NH)NH—C$_2$–C$_{12}$-alkenyl, —NHC(NH)NH—C$_2$–C$_{12}$-alkenyl, —NHC(NH)NH—C$_3$–C$_{12}$-cycloalkyl, —NHC(NH)NH-aryl, —NHC(NH)NH-heteroaryl, —NHC(NH)NH-heterocycloalkyl, NHC(NH)—C$_1$–C$_{12}$-alkyl, —NHC(NH)—C$_2$–C$_{12}$-alkenyl, —NHC(NH)—C$_2$–C$_{12}$-alkenyl, —NHC(NH)—C$_3$–C$_{12}$-cycloalkyl, —NHC(NH)-aryl, —NHC(NH)-heteroaryl, —NHC(NH)-heterocycloalkyl, —C(NH)NH—C$_1$–C$_{12}$-alkyl, —C(NH)NH—C$_2$–C$_{12}$-alkenyl, —C(NH)NH—C$_2$–C$_{12}$-alkenyl, —C(NH)NH—C$_3$–C$_{12}$-cycloalkyl, —C(NH)NH-aryl, —C(NH)NH-heteroaryl, —C(NH)NH-heterocycloalkyl, —S(O)—C$_1$–C$_{12}$-alkyl, —S(O)—C$_2$–C$_{12}$-alkenyl, —S(O)—C$_2$–C$_{12}$-alkenyl, —S(O)—C$_3$–C$_{12}$-cycloalkyl, —S(O)-aryl, —S(O)-heteroaryl, —S(O)-heterocycloalkyl-SO$_2$NH$_2$, —SO$_2$NH—C$_1$–C$_{12}$-alkyl, —SO$_2$NH—C$_2$–C$_{12}$-alkenyl, —SO$_2$NH—C$_2$–C$_{12}$-alkenyl, —SO$_2$NH—C$_3$–C$_{12}$-cycloalkyl, —SO$_2$NH-aryl, —SO$_2$NH-heteroaryl, —SO$_2$NH-heterocycloalkyl, —NHSO$_2$—C$_1$–C$_{12}$-alkyl, —NHSO$_2$—C$_2$–C$_{12}$-alkenyl, —NHSO$_2$—C$_2$–C$_{12}$-alkenyl, —NHSO$_2$—C$_3$–C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$–C$_{12}$-cycloalkyl, -methoxymethoxy, -methoxyethoxy, —SH, —S—C$_1$–C$_{12}$-alkyl, —S—C$_2$–C$_{12}$-alkenyl, —S—C$_2$–C$_{12}$-alkenyl, —S—C$_3$–C$_{12}$-cycloalkyl, —S-aryl, —S-heteroaryl, —S-heterocycloalkyl, or methylthiomethyl.

The term "C$_1$–C$_6$ alkoxy," as used herein, refers to a C$_1$–C$_6$ alkyl group, as previously defined, attached to the parent molecular moiety through an oxygen atom. Examples of C$_1$–C$_6$-alkoxy include, but are not limited to, methoxy, ethoxy, propoxy, isopropoxy, n-butoxy, tert-butoxy, neopentoxy and n-hexoxy.

The term "C$_1$–C$_3$-alkyl-amino," as used herein, refers to one or two C$_1$–C$_3$-alkyl groups, as previously defined, attached to the parent molecular moiety through a nitrogen atom. Examples of C$_1$–C$_3$-alkyl-amino include, but are not limited to, methylamino, dimethylamino, ethylamino, diethylamino, and propylamino.

The term "alkylamino" refers to a group having the structure —NH(C$_1$–C$_{12}$ alkyl) where C$_1$–C$_{12}$ alkyl is as previously defined.

The term "dialkylamino" refers to a group having the structure —N(C$_1$–C$_{12}$ alkyl) (C$_1$–C$_{12}$ alkyl), where C$_1$–C$_{12}$ alkyl is as previously defined. Examples of dialkylamino are, but not limited to, dimethylamino, diethylamino, methylethylamino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH(C$_1$–C$_{12}$ alkyl) or —C(O)N(C$_1$–C$_{12}$ alkyl)(C$_1$–C$_{12}$ alkyl), —C(O)NH$_2$, and the like.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, *Protective Groups in Organic Synthesis*, 3rd edition, John Wiley & Sons, New York (1999). Examples of hydroxy protecting groups include, but are not limited to, methylthiomethyl, tert-butyl-dimethylsilyl, tert-butyldiphenylsilyl, acyl substituted with an aromatic group and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, Protective Groups in Organic Synthesis, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

"An effective amount," as used herein, refers to an amount of a compound which confers a therapeutic effect on the treated subject. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1–19 (1977). The salts can be prepared in situ du ring the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesutfonate, formate, fumarate, glucoheptonate, glycerophosphate, gluconate, hemisulfate, heptanoate, hexanoate, hydroiodide, 2-hydroxy-ethanesuffonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

As used herein, unless otherwise indicated, the term "bacterial infection(s)" or "protozoa infections"; includes, but is not limited to, bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include, but are not limited to, the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus*, or Peptostreptococcus spp. Pseudomonas spp.; pharyingitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *S. pyogenes, S. agalactiae*, Streptococcal groups C–F (minute-colony streptococci), *viridans* streptococci, Corynebacterium spp., Clostridium spp., or *Bartonella henselae*; uncomplicated acute urinary tract infections related to infection by *S. saprophyticus* or Enterococcus spp.; urethritis and cervicitis; and sexually transmitted diseases related to infection by *Chlamydia trachomatis, Haemophilus ducreyi, Treponema pallidum, Ureaplasma urealyticum*, or *Nesseria gonorrheae*; toxin diseases related to infection by *S. aureus* (food poisoning and Toxic shock syndrome), or Groups A, S, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae*, or Listeria spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by Cryptosporidium spp. odontogenic infection related to infection by *viridans* streptococci; persistent cough related to infection by *Bordetella pertussis*; gas gangrene related to infection by *Clostridium perfringens* or Bacteroides spp.; Skin infection by *S. aureus*, Propionibacterium acne; atherosclerosis related to infection by *Helicobacter pylori* or *Chlamydia pneumoniae*; or the like.

Bacterial infections and protozoa infections and disorders related to such infections that may be treated or prevented in animals include, but are not limited to, the following: bovine respiratory disease related to infection by *P. haemolytica., P. multocida, Mycoplasma bovis*, or Bordetella spp.; cow enteric disease related to infection by *E. coli* or protozoa (i.e., coccidia, cryptosporidia, etc.), dairy cow mastitis related to infection by *S. aureus, S. uberis, S. agalactiae, S. dysgalactiae*, Klebsiella spp., Corynebacterium, or Enterococcus spp.; swine respiratory disease related to infection by *A. pleuropneumoniae., P. multocida*, or Mycoplasma spp.; swine enteric disease related to infection by *E. coli, Lawsonia intracellularis*, Salmonella spp., or *Serpulina hyodyisinteriae*; cow footrot related to infection by Fusobacterium spp.; cow metritis related to infection by *E. coli*; cow hairy warts related to Infection by *Fusobacterium necrophorum* or *Bacteroides nodosus*; cow pink-eye related to infection by *Moraxella bovis*, cow premature abortion related to infection by protozoa (i.e. neosporium); urinary tract infection in dogs and cats related to infection by *E. coli*; skin and soft tissue infections in dogs and cats related to infection by *S. epidermidis, S. intermedius*, coagulase neg. Staphylococcus or *P. multocida*; and dental or mouth infections in dogs and oats related to infection by Alcaligenes spp., Bacteroides spp., Clostridium spp., Enterobacter spp., Eubacterium spp., Peptostreptococcus spp., Porphfyromonas spp., Campylobacter spp., Actinomyces spp., Erysipelothrix spp., Rhodococcus spp., Trypanosoma spp., Plasodium spp., Babesia spp., Toxoplasma spp., Pneumocystis spp., Leishmania spp., and Trichomonas spp. or Prevotella spp. Other bacterial infections and protozoa infections and disorders related to such infections that may be treated or prevented in accord with the method of the present invention are referred to in J. P. Sanford at al., "The Sanford Guide To Antimicrobial Therapy," 26th Edition, (Antimicrobial Therapy, Inc., 1996).

Antibacterial Activity

Susceptibility tests can be used to quantitatively measure the in vitro activity of an antimicrobial agent against a given bacterial isolate. Compounds were tested for in vitro antibacterial activity by a micro-dilution method. Minimal Inhibitory Concentration (MIC) was determined in 96 well microtiter plates utilizing the appropriate Mueller Hinton Broth medium (CAMHB) for the observed bacterial isolates. Antimicrobial agents were serially diluted (2-fold) in DMSO to produce a concentration range from about 64 $\mu$g/ml to about 0.03 $\mu$g/ml. The diluted compounds (2 $\mu$l/well) were then transferred into sterile, uninoculated CAMHB (0.2 mL) by use of a 96 fixed tip-pipetting station. The inoculum for each bacterial strain was standardized to $5 \times 10^5$ CFU/mL by optical comparison to a 0.5 McFarland turbidity standard. The plates were inoculated with 10 $\mu$l/well of adjusted bacterial inoculum. The 96 well plates were covered and incubated at 35+/−2° C. for 24 hours in ambient air environment. Following incubation, plate wells were visually examined by Optical Density measurement for the presence of growth (turbidity). The lowest concentration of an antimicrobial agent at which no visible growth occurs was defined as the MIC. The compounds of the invention generally demonstrated an MIC in the range from about 64 µg/ml to about 0.03 µg/ml.

All in vitro testing follows the guidelines described in the Approved Standards M7-A4 protocol, published by the National Committee for Clinical Laboratory Standards (NCCLS).

Pharmaceutical Compositions.

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrastemal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringers solution, U.S.P. and isotonic sodium chloride solution. In addition, sterile, fixed oils are conventionally employed as a solvent or suspending medium. For this purpose any bland fixed oil can be employed including synthetic mono-or diglyceddes. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearale, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or other animals by administering to the patient a therapeutically effective amount of a compound of the invention, in such amounts and for such time as is necessary to achieve the desired result.

By a "therapeutically effective amount" of a compound of the invention is meant a sufficient amount of the compound to treat or prevent bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

The pharmaceutical compositions of this invention can be administered orally to fish by blending said pharmaceutical compositions into fish feed or said pharmaceutical compositions may be dissolved in water in which infected fish are placed, a method commonly referred to as a medicated bath. The dosage for the treatment of fish differs depending upon the purpose of administration (prevention or cure of disease) and type of administration, size and extent of infection of the fish to be treated. Generally, a dosage of 5–1000 mg, preferably 20–100 mg, per kg of body weight of fish may be administered per day, either at one time or divided into several times. It will be recognized that the above-specified dosage is only a general range which may be reduced or increased depending upon the age, body weight, condition of disease, etc. of the fish.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which may appear in the following synthetic schemes and examples are:

Ac for acetyl;
AIBN for azobisisobutyronitrile;
9-BBN for 9-borabicyclo[3.3.13]nonane;
Boc for tert-butoxycarbonyl;
Bu$_3$SnH for tributyltin hydride;
Bz for benzyl;
CDI for carbonyidiimidazole;
dba for dibenzylidene acetone;
DBU for 1,8-diazabicyclo[5.4.0]undec-7ene;
DEAD for diethylazodicarboxylate;
Dess-Martin periodinane for 1,1,1-tris(acetyloxy)-1,1-dihydro-1,2-benziodoxol-3-(1H)-one;
DMAP for dimethylaminopyridine;
DMF for dimethyl formamide;
DMSO for dimethyl sulfoxide;
DPPA for diphenylphosphoryl azide;
dppb for diphenylphosphino butane;
EtOAc for ethyl acetate;
iPrOH for isopropanol;
NaHMDS for sodium bis(trimethylsilyl)amide;
NMO for N-methylmorpholine N-oxide;
MeOH for methanol;
MOM for methoxymethyl;
PDC for pyridinium dichromate;
Ph for phenyl;
POPd for dihydrogen dichlorobis(di-tert-butylphosphino) palladium(II);
TBAHS for tetrabutyl ammonium hydrogen sulfate;
TBS for tert-butyl dimethylsilyl;
TEA for triethylamine;
THF for tetrahydrofuran;
TMS for trimethyl silyl;
TPAP for tetra-n-propyl ammonium perruthenate;
TPP for triphenylphosphine; and
Tris for Tris(hydroxymethyl)aminomethane.

Synthetic Methods

The compounds and processes of the present invention will be better understood in connection with the following synthetic schemes that illustrate the methods by which the compounds of the invention may be prepared.

A preferred intermediate for the preparation of compounds represented by formula I is a compound represented by the formula Ia:

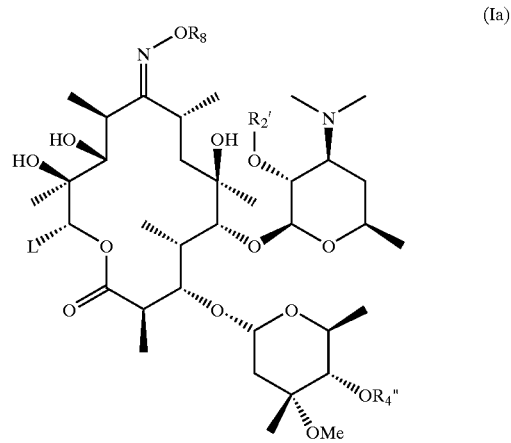

(Ia)

wherein

1) $R^8$ is
   a. hydrogen,
   b. —CH$_2$O(CH$_2$)$_2$OCH$_3$,
   c. —CH$_2$O(CH$_2$O)$_n$CH$_3$, where n is as previously defined;
   d. —C$_1$–C$_{12}$ alkyl, optionally substituted with one or more substituents selected from aryl, substituted aryl, heteroaryl and substituted heteroaryl;
   e. —C$_3$–C$_{12}$ cycloalkyl;
   f. —C(O)—C$_1$–C$_{12}$ alkyl;
   g. —C(O)—C$_3$–C$_{12}$ cycloalkyl;
   h. —C(O)—R$_1$, where R$_1$ is as previously defined; or
   i. —Si(R$_a$)(R$_b$)(R$_c$), wherein R$_a$, R$_b$ and R$_c$ are each independently selected from C$_1$–C$_{12}$ alkyl, aryl and substituted aryl; and 2) L, R$_2$', and R$_4$" are as previously defined.

A second preferred intermediate for the preparation of compounds represented by formula I is a compound represented by the formula Ib

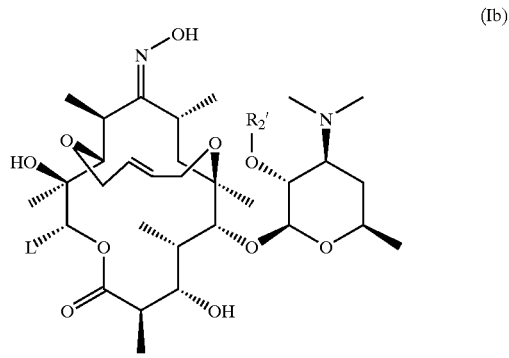

(Ib)

wherein L and R$_2$' are as previously defined.

Scheme 1

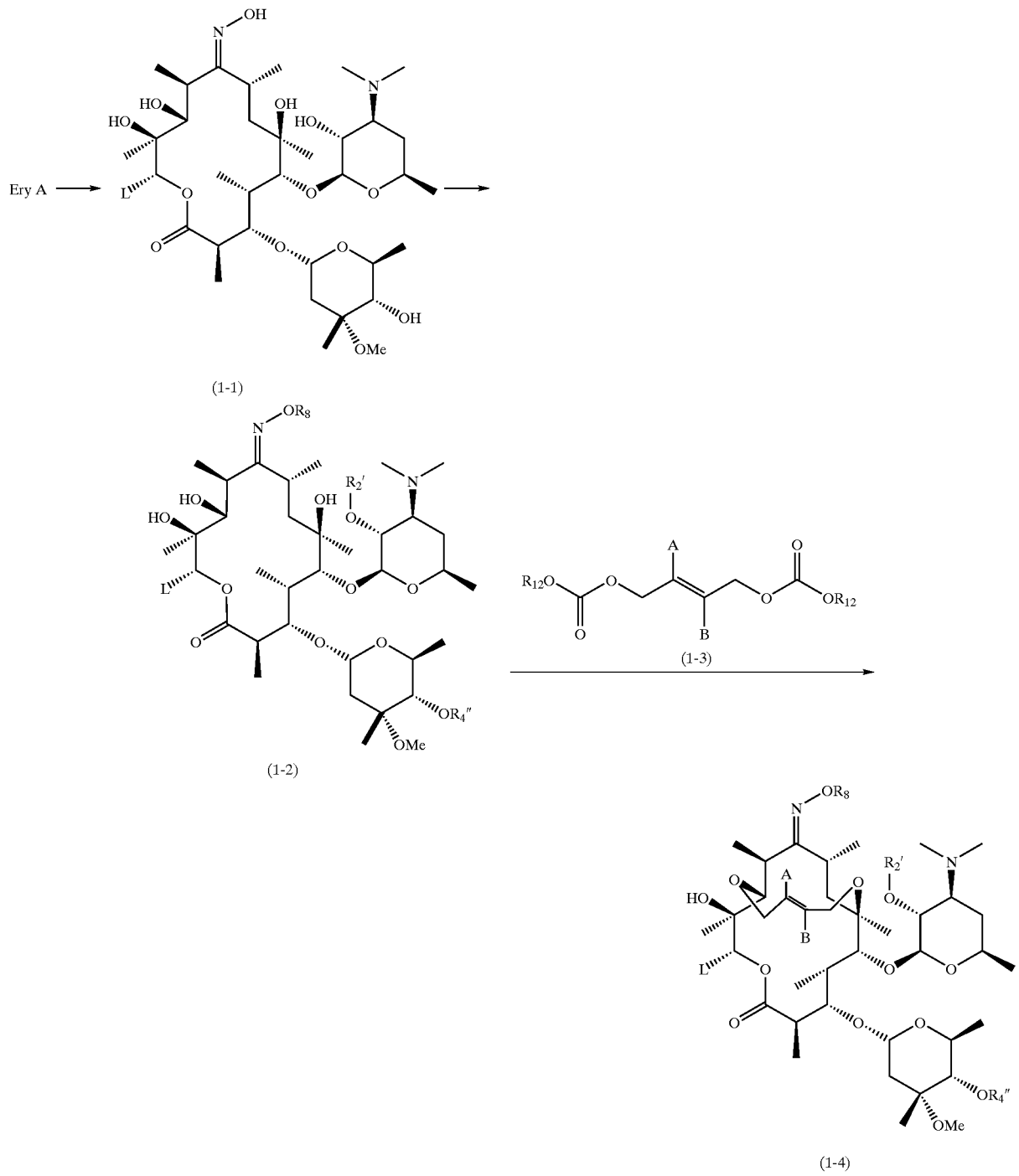

A process of the invention, as illustrated in Scheme 1, involves preparing a compound of formula (1-4) by reacting a compound of formula (1-2) with a suitable alkylating agent.

In accordance with Scheme 1, the 9-keto group of erythromycins can be initially converted into an oxime by methods described in U.S. Pat. No. 4,990,602, followed by the protection of the 2'- and 4"-hydroxyl and, if desired, the oxime groups of the erythromycin derivatives to obtain the compounds of formula (1-2).

The preparation of protected erythromycins is also described in U.S. Pat. Nos. 4,990,602; 4,331,803; 4,680,386, 4,670,549, European Patent Application No. EP 260,938.

The 2'- and 4"-hydroxyl groups are protected by reaction with suitable hydroxyl protecting reagents in an aprotic solvent. Typical hydroxyl protecting reagents include, but are not limited to, acetylating agents, silylating agents, acid anhydrides, and the like. Examples of hydroxyl protecting reagents are, for example, acetyl chloride, acetic anhydride, benzoyl chloride, benzoic anhydride, benzyl chloroformate, hexamethyldisilazane, and trialkylsilyl chlorides.

Examples of aprotic solvents are dichloromethane, chloroform, tetrahydrofuran, N-methylpyrrolidinone, dimethylsulfoxide, N,N-dimethylformamide, N,N-dimethylacetamide, hexamethylphosphoric triamide, a mixture thereof or a mixture of one of these solvents with ether, tetrahydrofuran, 1,2-dimethoxyethane, 1,2-dichloroethane, acetonitrile, ethyl acetate, acetone and the like. Aprotic solvents do not adversely affect the reaction. Preferably, the solvent is selected from dichloromethane, chloroform, N,N-dimethylformamide, tetrahydrofuran, N-methylpyrrolidinone or mixtures thereof. A more thorough discussion of solvents and conditions for protecting the hydroxyl group can be found in T. W. Greene and P. G. M. Wuts, *Protective Groups in Organic Synthesis*, 3$^{rd}$ ed., John Wiley & Son, Inc, 1999.

Protection of 2'- and 4"-hydroxyl groups may be accomplished sequentially or simultaneously to provide compound (1-2) where $R_2$' and/or $R_4$" can be, for example, acetyl, benzoyl, trimethylsilyl, and the like. Preferred protecting groups include acetyl, benzoyl, and trimethylsilyl. A particularly preferred group for protecting the hydroxyl and oxime groups is the benzyl protecting group, wherein $R_2$'=$R_4$"=$R_8$=Bz.

Benzoylation of the $R_2$' and $R_4$" and $R_8$ hydroxy groups can be achieved through treatment with benzoic anhydride in THF in the presence of triethylamine and DMAP.

The erythromycin derivative of formula (1-2) is then reacted with an alkylating agent of the formula:

$$R_{12}\text{—OC(O)O—CH}_2\text{C(A)}=\text{C(B)CH}_2\text{—OC(O)—OR}_{12} \quad (1\text{-}3),$$

wherein $R_{12}$ is $C_1$–$C_{12}$-alkyl and $R_{11}$ is as previously defined.

Most palladium (0) catalysts are expected to work in this process. Some palladium (II) catalysts, such as palladium (II) acetate, which is converted into a palladium (0) species in-situ by the actions of a phosphine, will work as well. See, for example, Beller et al. *Angew. Chem. Int. Ed. Engl.*, 1995, 34 (17), 1848. The palladium catalyst can be selected from, but not limited to, palladium (II) acetate, tetrakis(triphenylphosphine)palladium (0), tris(dibenzylideneacetone)dipalladium, tetradibenzylideneacetone)dipalladium and the like. Palladium on carbon and palladium (II) halide catalysts are less preferred than other palladium catalysts for this process. Suitable phosphines include, but are not limited to, triphenylphosphine, bis(diphenylphosphino)methane, bis(diphenylphosphino)ethane, bis(diphenylphosphino)propane, 1,4-bis(diphenylphosphino)butane, bis(diphenylphosphino)pentane, and tri-o-tolyl-phosphine, and the like. The reaction is carried out in anaprotic solvent, preferably at elevated temperature, preferably at or above 50° C. Suitable aprotic solvents include, but are not limited to, tetrahydrofuran, N,N-dimethylformamide, dimethyl sulfoxide, N-methyl-2-pyrrolidone, hexamethylphosphoric triamide, 1,2-dimethoxyethane, methyl-tert-butyl ether, heptane, acetonitrile, isopropyl acetate and ethyl acetate. The most preferred solvents are tetrahydrofuran or toluene.

Generally, the alkylating agents have the formula (1-3) as previously described. The preferred alkylating agents are those wherein $R_{12}$ is tert-butyl, isopropyl or isobutyl. The alkylating reagents are prepared by reaction of a diol with a wide variety of compounds for incorporating the di-carbonate moiety. The compounds include, but are not limited to, tert-butyl chloroformate, di-tert-butyl dicarbonate, and 1-(tert-butoxycarbonyl)imidazole and the reaction is carried out in the presence of an organic or an inorganic base. The temperature of the reaction varies from about –30° C. to approximately 30° C. Preferably the alkylating reagent is di-tert-butyl dicarbonate.

An alternative method of converting the alcohol into the carbonate involves treating the alcohol with phosgene or triphosgene to prepare the chloroformate derivative of the diol. The di-chloroformate derivative is then converted into the di-carbonate by the methods described in Cotarca, L., Delogu, P., Nardelli, A., Sunijic, V, *Synthesis*, 1996, 553. The reaction can be carried out in a variety of organic solvents such as dichloromethane, toluene, diethyl ether, ethyl acetate and chloroform in the presence of a base. Examples of suitable bases include, but are not limited to, sodium hydroxide, potassium hydroxide, ammonium hydroxide, sodium carbonate, potassium carbonate, ammonium carbonate, DMAP, pyridine, triethylamine and the like. The temperature can vary from 0° C. to approximately 60° C. The reaction runs to completion in 3 to 5 hours.

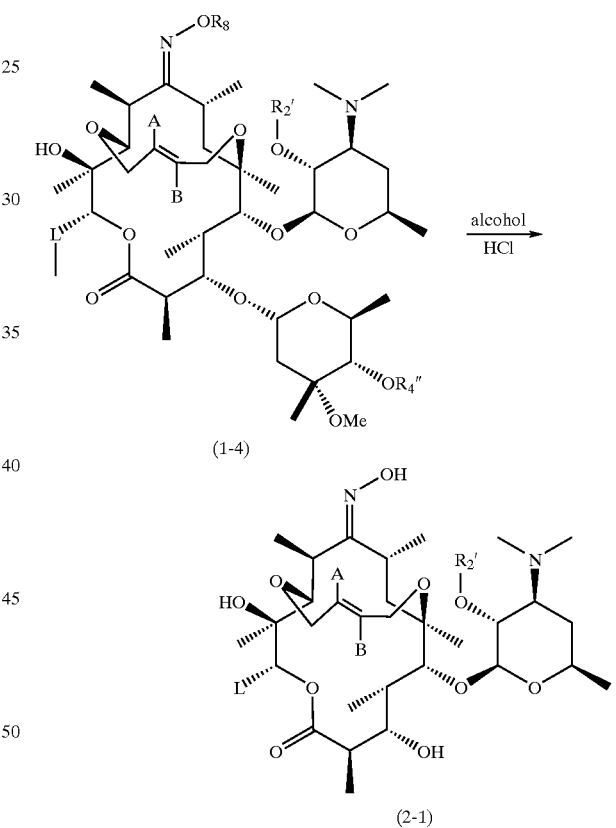

Another process of the invention involves the removal of the cladinose moiety of the compounds of formula 1. The cladinose moiety of the macrolide compound (1-4) is removed either by mild acid hydrolysis or by enzymatic hydrolysis to afford compounds of formula (2-1) in Scheme 2. Representative acids include, but are not limited to, dilute hydrochloric acid, sulfuric acid, perchloric acid, chloroacetic acid, dichloroacetic acid or trifluoroacetic acid. Suitable solvents for the reaction include, but are not limited to, methanol, ethanol, isopropanol, butanol, water and mixtures there of. Reaction times are typically 0.5 to 24 hours. The reaction temperature is preferably 0 to 80° C.

Scheme 3

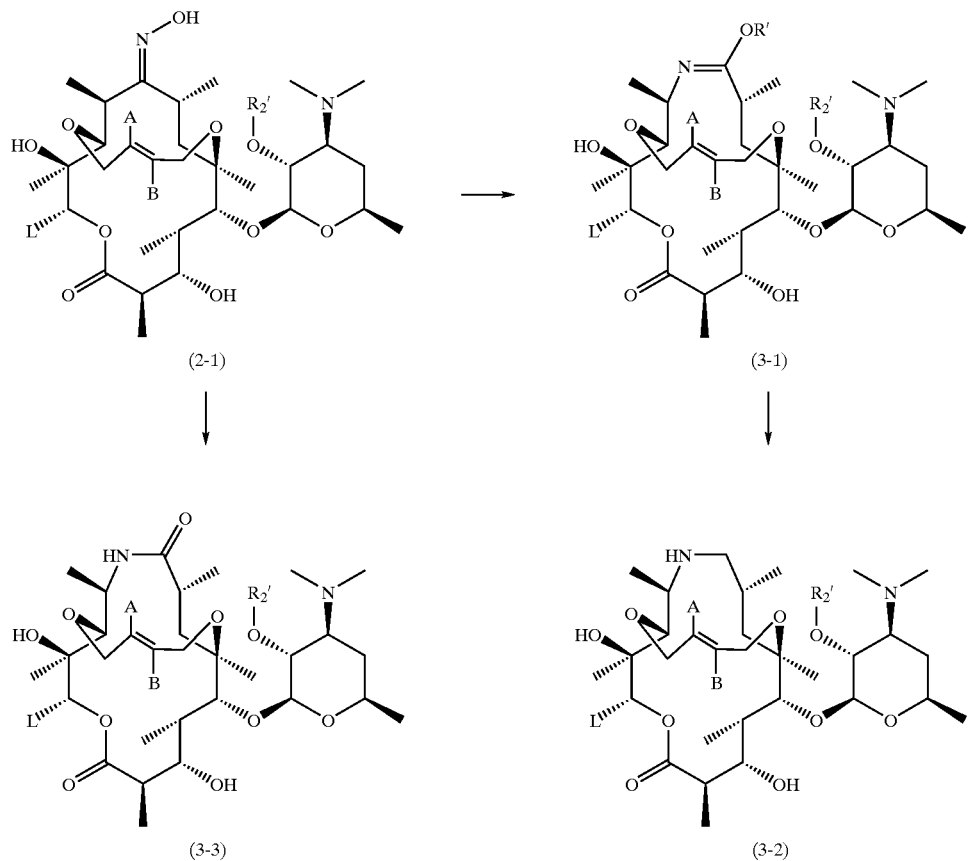

The compound of formula (2-1) where $R_2'$ is Ac can be converted into the compound of formula (3-1) and (3-3) by Beckmann rearrangement. Thus, the compound of formula (2-1) is treated with oxime activating agents and subsequently quenched by addition of alcohol of formula (R'OH, where R' is as previously defined) to provide the compounds of formula (3-1). Representative oxime activating agents include, but are not limited to, sulfonic anhydrides and sulfonyl halides such as p-toluenesulfonic anhydride, methanesulfonic anhydride, p-toluenesulfonyl chloride, methanesulfonyl chloride, p-bromosulfonyl chloride, optionally in the presence of a base such as, but not limited to, pyridine, triethyl amine, diisopropylethyl amine, $NaHCO_3$, $Na_2CO_3$, $KHCO_3$ and $K_2CO_3$. For further details concerning the Beckmann rearrangement see L. G. Donamima, W. Z. Heldt, Org. React. 11, 1–156 (1960); R. E. Gawley, ibid. 35, 1–420 (1988); C. G. McCarty in The Chemistry of the Carbon-Nitrogen Double Bond, S. Patai, Ed. (Interscience, New York, 1970) pp 408–439; J. R. Hauske, Comp. Org. Syn. 1, 98–100 (1991); K. Maruoka, H. Yamamoto, ibid. 6, 763–775; D. Craig, ibid. 7, 689–702.

Reduction of compounds of formula (3-1) to compounds of formula (3-2) can be achieved by treatment of the former with reducing agents including, but not limited to, borane in THF, borane dimethylsulfide, sodium cyanoborohydride, sodium borohydride optionally in the presence of an acid such as $TiCl_4$, $COCl_2$, $AlCl_3$, methanesulfonic acid, or acetic acid. Solvents which are applicable include, but are not limited to, tetrahydrofuran, 1,4-dioxane, 1,2-dimethoxyethane, isopropanol, ethanol, butanol, acetonitrile, diethyl ether, dichloromethane, water and mixtures thereof. The reaction temperature is –78° C. to 30° C. In a particularly preferred embodiment, compounds of formula (2-1) are treated with p-toluenesulfonic anhydride and triethylamine in methylene chloride and subsequently quenched with methanol to provide compounds of formula (3-1). Compounds of formula (3-1) are then treated with $NaBH_4$ in methanol to provide the compounds of formula (3-2). The compounds of formula (3-3) were synthesized via treatment of compounds of formula (2-1) with p-toluenesulfonyl chloride and $NaHCO_3$ in acetone and water.

Scheme 4

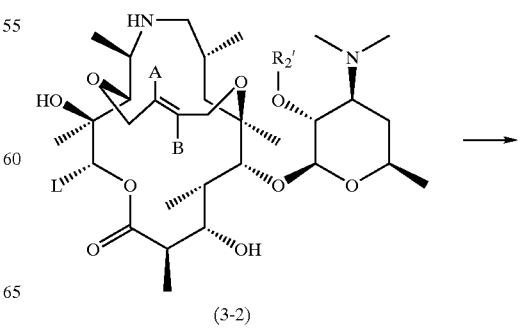

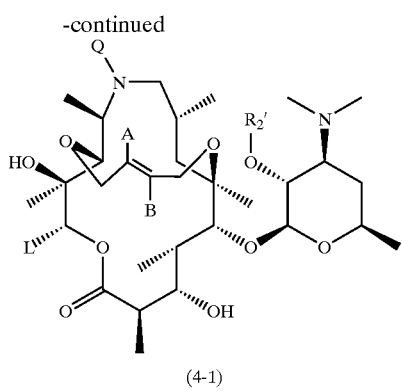

(4-1)

Compounds of formula (3-2) can be converted to compounds of formula (4-1) by treatment of the former with alkylating agent Q-$X_1$, wherein $X_1$ is a halo leaving group, in the presence of base. An alternative means of converting compounds of formula (3-2) to compounds of formula (4-1) is treatment of the compounds of formula (3-2) with an aldehyde Q—CHO in the presence of acetic acid and excess $NaCNBH_3$ to provide compounds of formula (4-1) where a is —$CH_2R_2$, wherein $R_2$ is as previously defined. Examples of solvents include, but are not limited to, acetonitrile, diethylether, dichloromethane, chloroform, ethyl acetate, THF, dioxane or mixtures thereof. The reaction generally proceeds at from −20° C. to 80° C. for 30 minutes to 18 hours. In a particularly preferred embodiment, Q—CHO is reacted with (3-2) in chloroform at 80° C.

Scheme 5

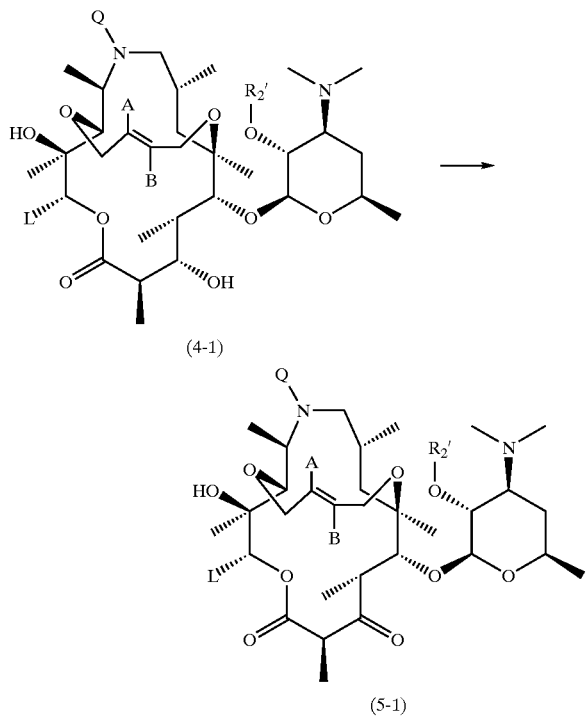

Conversion of compounds of formula (4-1) to compounds of formula (5-1) can be accomplished by oxidation of the 3-hydroxy group to a 3-oxo group using Dess-Martin periodinane (for further details concerning the Dess-Martin oxidation see D. B. Dess, J. C. Martin, *J. Org. Chem.* 48, 4155 (1983)), a Corey-Kim reaction with N-chlorosuccinimide-dimethylsulfide (for further details concerning the Corey-Kim oxidation reaction see E. J. Corey, C. U. Kim, *J. Am. Chem. Soc.* 94, 7586 (1972)), or a Moffat oxidation with a carbodiimide-DMSO complex in the presence of pyridinium trifluoroacetate, TPAP, PDC, and the like (for further details concerning the Moffat oxidation see J. G. Moffatt, "Sulfoxide-Carbodiimide and Related Oxidations" in *Oxidation* vol. 2, R. L. Augustine, D. J. Trecker, Eds. (Dekker, N.Y., 1971) pp 1–64; T. T. Tidwell, *Org. React.* 39, 297–572 passim (1990); and T. V. Lee, *Comp. Org. Syn.* 7, 291–303 passim (1991)). In a preferred embodiment, compounds of formula (4-1) are treated with Dess-Martin periodinane in dichloromethane at about 0° C. to about 25° C for approximately 0.5 to 4 hours to produce compounds of formula (5-1).

Scheme 6

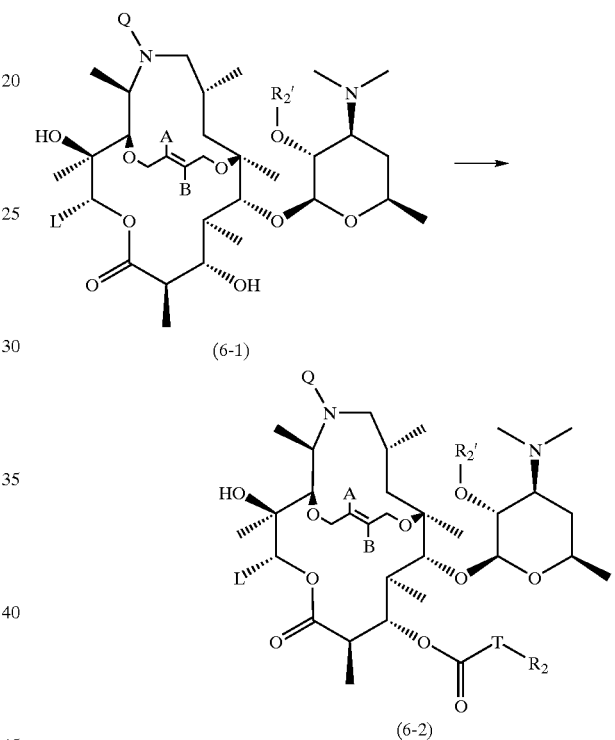

Scheme 6 illustrates a procedure for the acylation of the C-3 hydroxy group of compounds of formula (6-1). The C-3 hydroxy group is acylated under basic conditions using a suitable acylating agent to introduce the acyl group of the formula —C(O)—T—$R_2$, where T is O, N, S or —$(CH_2)_t$, where t=0 to 4 and $R_2$ is as previously described, in an aprotic solvent as previously described for acylating compounds of formula (3-2). Typical acylating agents include, but are not limited to, acid halides, acid anhydrides, free acids and chloroformates. Typical bases include, but are not limited to, pyridine, DMAP, triethylamine, diisopropyl ethylamine, N-methyl morpholine, N-methyl pyrrolidine, 2,6-lutidine, 1,8-diazabicyclo[5.4.0]undec-7-ene. (See, T. W. Greene and P. G. M. Wuts in Protective Groups in Organic Synthesis $3^{rd}$ ed., John Wiley & Son, Inc, 1999, and references therein).

Alternately, in compounds of formula (6-1) the C-3 hydroxy group may be further derivatized to form, for example, ethers, esters, sulfonates, and the like, using methods well known in the art (see, for example, J. March, *Advanced Organic Chemistry* $4^{th}$ ed., Wiley & Son, Inc., 1992, and the references therein).

Scheme 7

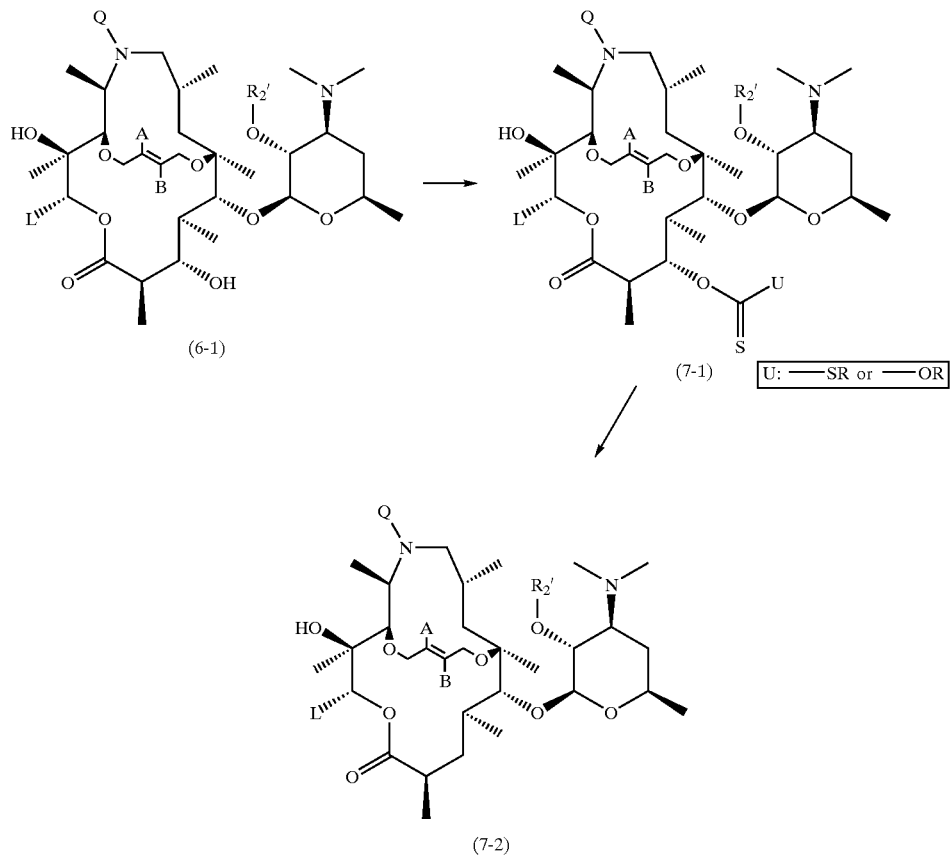

Another method of the present invention, as illustrated in Scheme 7, involves synthesis of the C-3 deoxygenated macrolide (7-2) which can be accomplished via the two step procedure shown above. In the first step, the xanthate or thiocarbonate of formula (7-1) is formed by the reaction of alcohol of formula (6-1) with the appropriate thiocarbonyl compound. These reactions are typically run in a polar aprotic solvent, preferably tetrahydrofuran, acetonitrile, N,N-dimethylformamide, and the like. Formation of the xanthate can be accomplished, for example, by reaction of the alcohol (6-1) with, for example, but not limited to, carbondisulfide followed by methyliodide, or a dithiocarbonyl imidazole etc. The thiocarbonate can be prepared by the reaction of the alcohol with for example, but not limited to, thiocarbonyldimidazole followed by methanol, ethanol or the like, or a thiochloroformate etc. One skilled in the art will appreciate that other reagents and conditions exist to perform these transformations and that the examples above are for illustrative purposes only and do not limit the scope of this invention.

In the second step, the thiocarbonate or xanthate of formula (7-1) is converted to compound (7-2). Most typically this is done under radical conditions using, for example, a silyl hydride such as $SiH(TMS)_3$, $SiH_2Ph_2$ or the like, a tin hydride such as $Bu_3SnH$, $Ph_3SnH$ or the like, and a radical initiator such as AIBN or t-butyl peroxide. The preferred solvent is toluene.

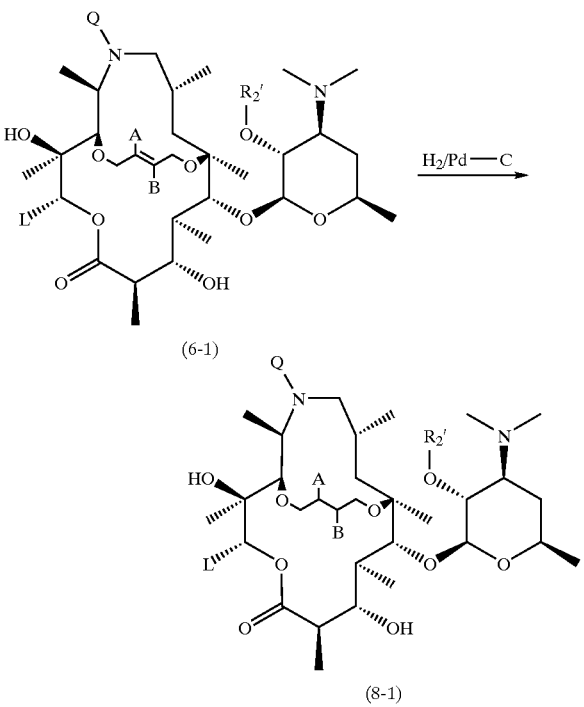

Compounds according to the formula (8-1) may be prepared from compounds of formula (6-1) by selective hydrogenation methods known in the art, for example, but not limited to, metal hydrides, such as, borane, or hydrogen in the presence of a catalyst, such as, palladium-on-charcoal, platinum metal or oxide, Wilkinson's catalyst and the like (see, Rylander, *Hydrogenation Methods*; Academic Press: New York, 1985; J. March, *Advanced Organic Chemistry* $4^{th}$ ed., Wiley & Son, Inc., 1992; and the references therein).

J. Nitrones in 1,3 [*One, Three*]-*Dipolar Cycloaddit. Chem.* (1984), 2, 83–168. (b) Huisgen, Rolf. 1,3-*Dipolar cycloaddition—introduction, survey, mechanism* in 1,3 [*One, Three*]-*Dipolar Cycloaddit. Chem.* (1984), 1, 1–176, and the references therein). Compounds (9-2) and (9-3) can be prepared similarly by reacting compound (9-1) with an azide or a nitrone respectively.

Other 1,3-Dipolar cycloaddition reactants useful in forming cycloaddition products with compounds of the present Scheme 9

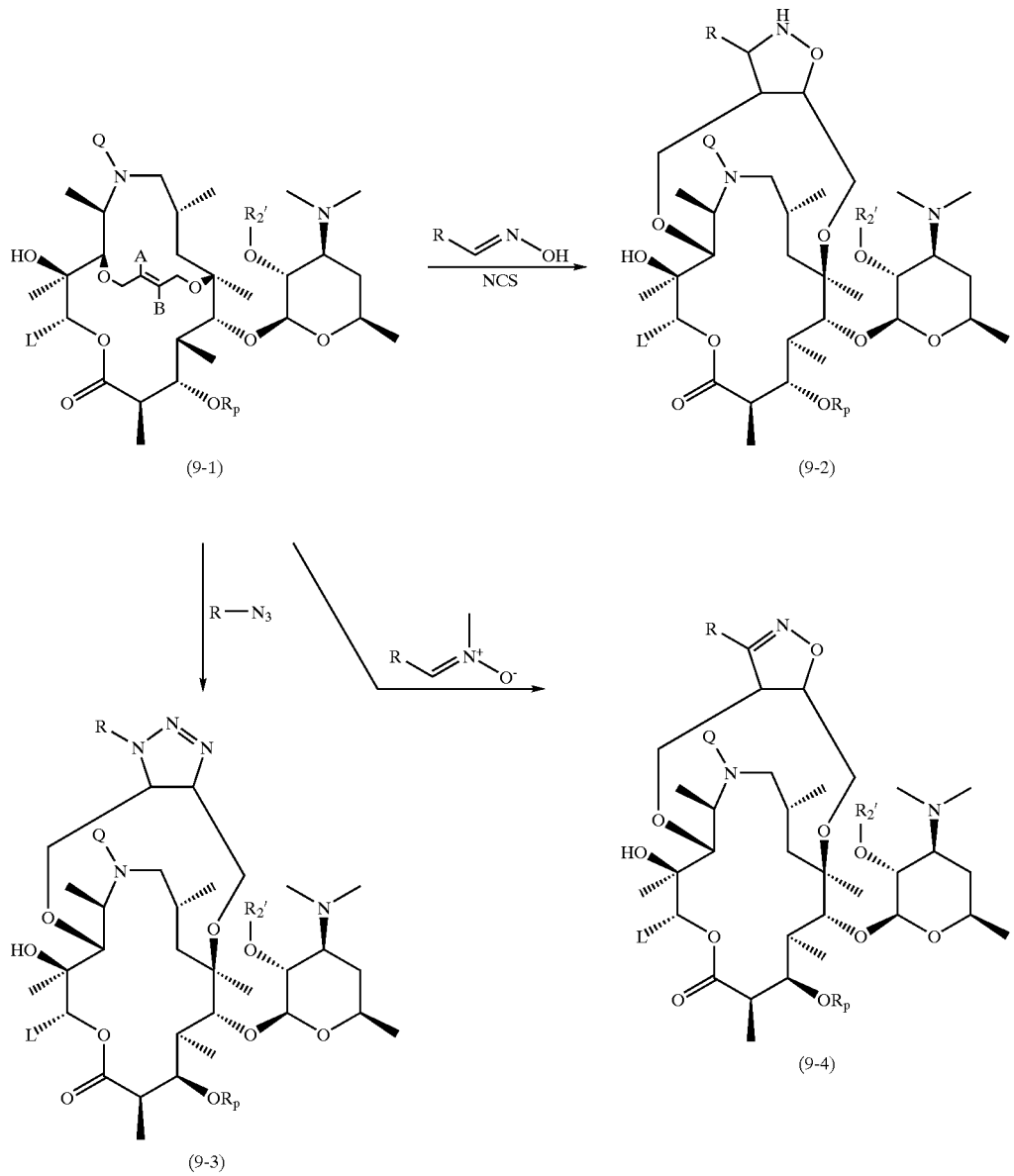

Compounds (9-2, 9-3 and 9-4, where R is $R_3$ as previously defined and $R_p$ and $R_2'$ are as previously defined) can be prepared by the well-established 1,3-dipolar cycloaddition reactions, such as, but not limited to, reaction of compound (9-1) and an oxime in the presence of NCS in an aprotic solvent such as ethyl acetate, methylene chloride, THF, or the like, to form compound (9-1) (see (a) Tufariello, Joseph invention such as compound (9-1) include, but are not limited to, diazoalkane, nitrous oxide, nitrile imine, nitrile ylide, nitrile oxide, etc. (see, Padwa 1,3-*Dipolar Cycloaddition Chemistry*, 2 vols.; Wiley: New York, 1984, and J. March, *Advanced Organic Chemistry*, $4^{th}$ edition; Wiley: New York, 1992, and the references therein).

Scheme 10

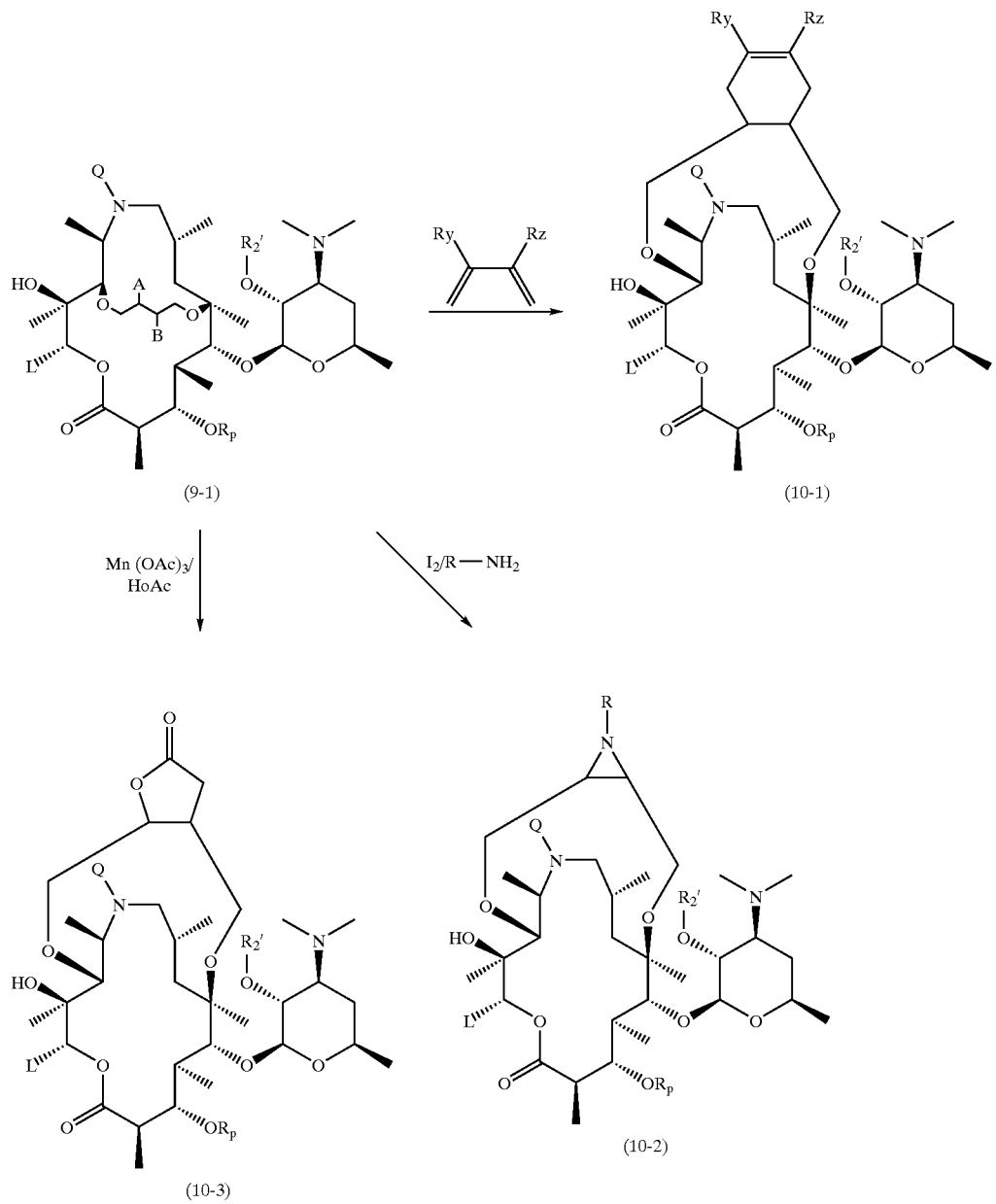

Compound (10-1) is prepared by Diels-Alder reactions, where $R_y$ and $R_z$ independently may be selected from CHO, COOH, COOR, COR, COAr, CN, $NO_2$, Ar, $CH_2OH$, $CH_2Cl$, $CH_2NH_2$, $CH_2CN$, $CH_2COOH$, halogen, —C≡C—, R and the like, R being $R_3$ as previously defined herein (see (a) Danishefsky, Samuel. *Cycloaddition and cyclocondensation reactions of highly functionalized dienes: applications to organic synthesis* in *Chemtracts: Org. Chem.* (1989), 2 (5), 273–97, (b) Larock *Comprehensive Organic Transformation*; VCH: New York, 1989, 263–272, and the references therein).

Aziridines such as compound (10-2) can be obtained from, for example, but not limited to, the reaction of compound (9-1) with iodine in the presence of a primary amine in an aprotic solvent such as methylene chloride, THF, and the like.

Lactones such as compound (10-3) can be obtained by a variety of reactions such as but not limited to, reaction with: manganese (III) acetate in the presence of acetic acid, lead tetraacetate, α-bromocarboxylic acids in the presence of benzoyl peroxide etc. (see, Larock *Comprehensive Organic Transformation*; VCH: New York, 1989; J. March, *Advanced Organic Chemistry*, 4th edition; Wiley: New York, 1992, and the references therein).

Scheme 11

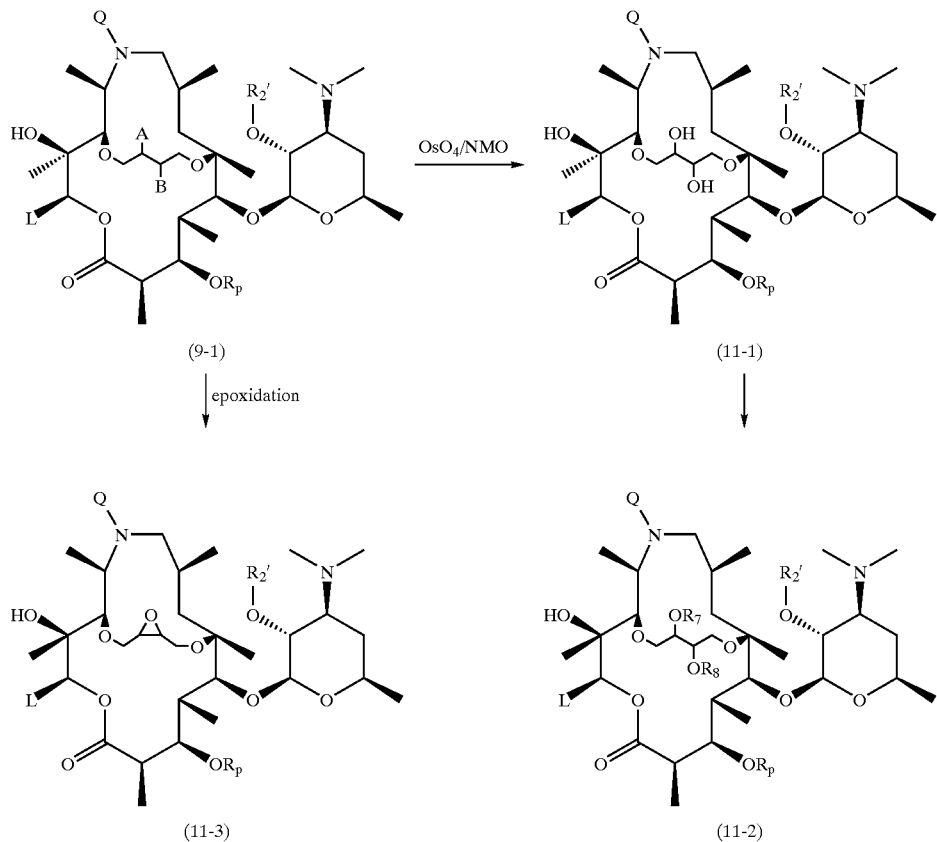

Compound (11-1) is prepared by osmium tetraoxide (OSO$_4$) catalyzed dihydroxylation of the double bond. In a typical procedure, compound (6-1) is treated with about 1 to about 3 equivalents of NMO in a solvent like t-butanol or acetone, with or without water, in the presence of about 1 to about 10% of 0504. Compound (11-2) can then be obtained from compound (11-3) through standard acylation or alkylation of the diol, where $R_7$ and $R_8$ are independently selected from $R_3$ and where $R_3$ is as previously defined herein.

Compound (11-3) is prepared by epoxidation of the double bond with reagents such as, but not limited to, peracids, e.g. m-CPBA, hydrogen peroxide, t-BuOOH etc. (see (a) *Chem. Rev.* 1989, 89, 431; (b) *Chem. Rev.* 1992, 92, 873, and references therein).

Scheme 12

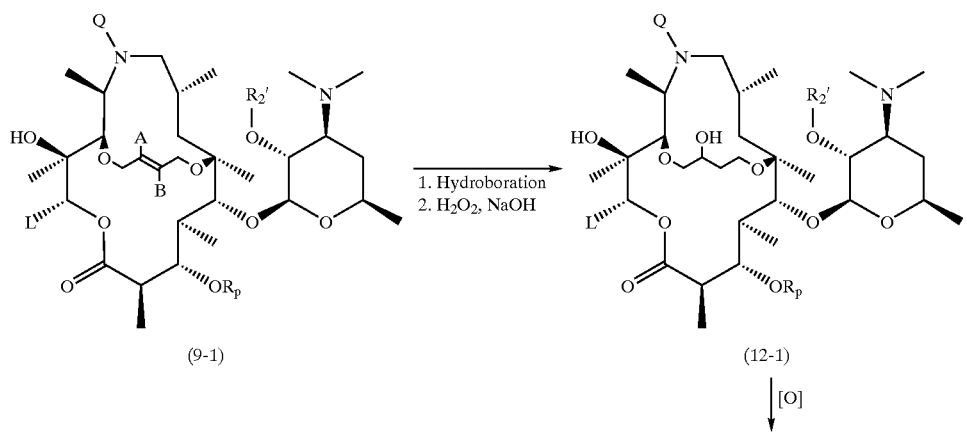

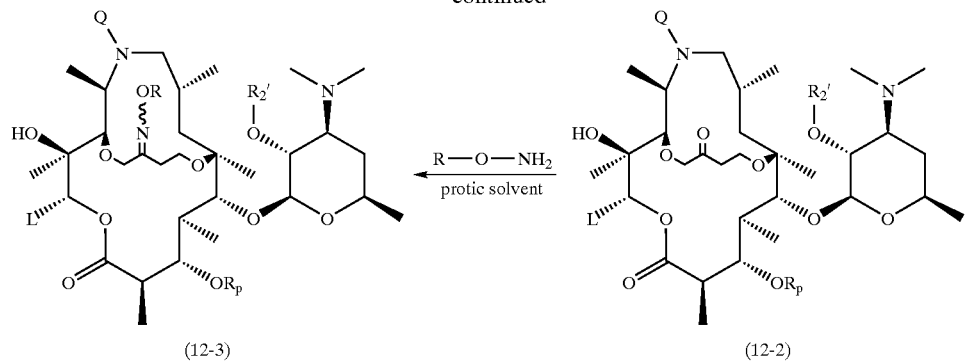

(12-3) (12-2)

Compounds of formula (9-1) can be converted to compounds of formula (12-1) by, for example, but not limited to, hydroboration with a borane reagent, for example, $B_2H_6$-THF, 9-BBN (9-borabicyclo[3.3.1]nonane), and the like, (optionally complexed with THF, dimethylsulfide, phosphines, tertiary amines and the like) and followed by treatment with hydrogen peroxide and NaOH.

Compounds of formula (12-1) may be oxidized to compounds of formula (12-2) with a suitable oxidizing agent. Compounds of formula (12-2) can be reacted with appropriate substituted hydroxylamines of the general formula $RONH_2$ where R is preferably $R_3$, where $R_3$ is as previously defined, in a protic solvent under acidic or basic conditions to give compounds of the formula (12-3). Representative acids include, but are not limited to, hydrochloric acid, phosphoric acid, sulfuric acid, p-toluenesulfonic acid, etc. Representative bases include, for example, triethylamine, pyridine, diisopropylethyl amine, 1,5-lutidine, and the like. Appropriate solvents include, but are not limited to, methanol, ethanol, water, tetrahydrofuran, 1,2-dimethoxyethane and ethyl acetate.

Also, compounds of the formula (12-2), where the ketone is on the 6,11-4-carbon bridge, may be further derivatized, for example, but not limited to, conversion to the corresponding amines by reductive amination, reaction with hydrazines to form the corresponding hydrazones, conversion to substituted alkenes by Wittig reaction, alkylation with Grignard reagent etc., by standard methods known in the art described in references incorporated herein.

Scheme 13

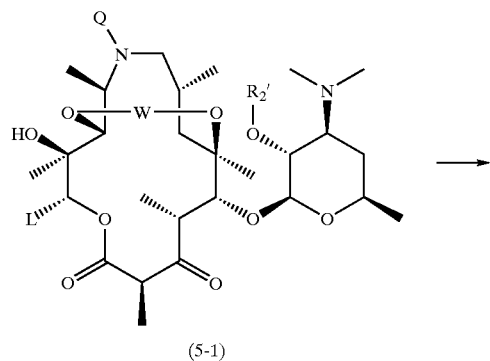

(5-1)

-continued (13-1)

Scheme 13 illustrates the procedure by which compounds of formula (5-1), wherein A, B, Q, and $R_2'$ are as previously defined, may be converted to compounds of formula (13-1), wherein Q, W, Z, and $R_2'$ are as previously defined, by treatment with a halogenating reagent. This reagent acts to replace a hydrogen atom with a halogen atom at the C-2 position of the ketolide. Various halogenating reagents may be suitable for this procedure.

Fluorinating reagents include, but are not limited to, N-fluorobenzenesulfonimide in the presence of base, 10% $F_2$ in formic acid, 3,5-dichloro-1-fluoropyridinium tetrafluoroborate, 3,5-dichloro-1-fluoropyridinium triflate, $(CF_3SO_2)_2NF$, N-fluoro-N-methyl-p-toluenesulfonamide in the presence of base, N-fluoropyridinium triflate, N-fluoroperfluoropiperidine in the presence of base.

Chlorinating reagents include, but are not limited to, hexachloroethane in the presence of base, $CF_3CF_2CH_2ICl_2$, $SO_2Cl_2$, $SOCl_2$, $CF_3SO_2Cl$ in the presence of base, $Cl_2$, NaOCl in the presence of acetic acid.

Brominating reagents include, but are not limited to, $Br_2$·pyridine·HBr, $Br_2$/acetic acid, N-bromosuccinimide in the presence of base, $LDA/BrCH_2CH_2Br$, or $LDA/CBr_4$.

A suitable iodinating reagent is N-iodosuccinimide in the presence of base, or $I_2$, for example.

Suitable bases for the halogenating reactions requiring them are compounds such as alkali metal hydrides, such as NaH and KH, or amine bases, such as LDA or triethylamine, for example. Different reagents may require different type of base, but this is well known within the art.

A preferred halogenating reagent is N-fluorobenzenesulfonimide in the presence of sodium hydride.

Suitable solvents are dimethylformamide, dimethyl sulfoxide, pyrrolidinone and the like.

It will be appreciated by one skilled in the art that all ketolide compounds delineated herein may be halogenated at the 2-carbon if so desired.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

EXAMPLE 1

Compound of formula I, wherein W is —$CH_2CH$=$CHCH_2$—, D=—N=CH(OMe)—, X=Z=H,

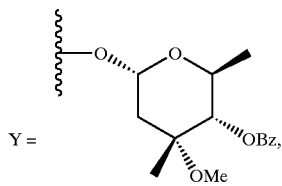

$L=CH_2CH_3$, and $R_2'$=Bz.

Step 1a:

A compound of formula (1-2), wherein $R_8=R_2'=R_4''$=Bz.

To a solution of erythrmycin A oxime (27.5 g, 36.7 mmol), benzoic anhydride (34.9 g, 154 mmol) in 200 ml THF is added triethylamine (22.5 ml, 161.6 mmol) and DMAP (4.49 g, 36.7 mmol) at room temperature and stirred for 24 hours. The reaction mixture is condensed to about 100 ml. Then ethyl acetate (300 ml) is added, and the resulting organic phase is washed with saturated $NaHCO_3$ (300 ml×3) and brine (300 ml×1). The organic phase is dried over anhydrous $Na_2SO_4$ and the solvent is removed in vacuo to give the title compound (90 g).

MS (ESI) m/z 1062.27 $(M+H)^+$

Step 1b:

Compound of formula (1-3)

To a solution of (9.25 g, 105 mmol) and di-tert-butyl dicarbonate (60 g, 275 mmol) in 150 ml of dichloromethane is added 6N NaOH (140 ml) and tetrabutylammonia hydrogensulfate (3.4 g, 10 mmol). The mixture is stirred at room temperature overnight. The organic layer is separated, washed with $NaHCO_3$ (200 ml×3) and brine(200 ml), dried over anhydrous $MgSO_4$, concentrated and dried over vacuum to give the title compound $^1H$ NMR ($CDCl_3$): 5.65(t, 2H); 4.54(d, 4H); 1.18(s, 18H).
$^{13}C$ NMR($CDCl_3$): δ153.3, 128.1, 82.4, 62.4, 27.8.

Step 1c:

Compound of formula (1-4), wherein $R_8=R_2'=R_4''$=Bz.

To a solution of erythromycin oxime 2', 4", 9-tribenzoate from Step 1a (5.31 g, 5 mmol), the compound from step 1b (4.33 g, 15 mmol) and dppb (213 mg, 0.5 mmol) in THF (40 ml), is added $Pd_2(dba)_3$ (229 mg, 0.25 mmol) under nitrogen. The mixture is refluxed for 1.5 hours and diluted with ethyl acetate (150 ml), washed with saturated $NaHCO_3$ (200 ml×2) and brine (200 ml), and dried over anhydrous $Na_2SO_4$. The solvent is removed in vacuo, and the residue is purified by flash chromatography ($SiO_2$ hexane:acetone/ 2:1) to give the title compound (5.0 g).

MS (ESI) m/z 1113.82 $(M+H)^+$

Step 1d:

A compound of formula (1-4), wherein $R_8$=OH and $R_2'=R_4''$=Bz.

To a solution of compound from step 1c (5.0 g, 4.5 mmol) in 40 ml isopropanol is added 1 M NaOH (5 ml) at 0° C. The mixture is stirred at that temperature for 30 minutes and then is quenched by addition of saturated $NaHCO_3$ (50 ml). The mixture is extracted with ethyl acetate (60 ml×1) and dried over anhydrous $Na_2SO_4$. The solvent is removed in vacuo, and the residue is purified via flash chromatography ($SiO_2$, hexane/acetone=4/1) to give the title compound (3.0 g).

MS (ESI) m/z 1009.86$(M+H)^+$.

$^{13}C$ NMR($CDCl_3$): δ176.4, 171.8, 166.5, 165.7, 165.5, 138.2, 133.6, 132.8, 131.1, 131.0, 130.2, 130.0, 128.6, 128.5, 100.8, 96.4, 80.5, 79.7, 79.3, 78.5, 77.5, 75.6, 73.3, 72.8, 71.7, 71.0, 68.0, 64.0, 63.6, 62.7, 60.6, 50.0, 45.2, 41.2, 39.7, 35.6, 35.4, 34.7, 32.2, 27.2, 23.0, 21.6, 21.5, 21.3, 20.8, 20.7, 18.5, 18.2, 15.8, 15.5, 14.4, 11.3, 9.8.

Step 1e:

Compound of formula I, wherein W is —$CH_2CH$=$CHCH_2$—. D=

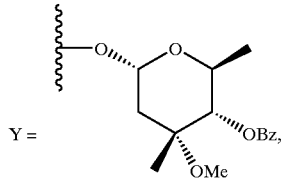

$L=CH_2CH_3$, and $R_2'$=Bz.

To a solution of the compound from step 1d (10 mg, 0.1 mmol) in $CH_2Cl_2$ (5 ml) at −10° C. is added p-toluenesulfonic anhydride. (43 mg, 0.13 mmol, 1.3 eq) is added to a solution of compound of step 1d (101 mg, 0.1 mmol) and anhydrous $Et_3N$ (21 μl, 0.15 mmol). The resulting mixture is stirred at −10° C. for 40 min. Anhydrous MeOH (4 mL) is added to the reaction mixture at −10° C. and the reaction mixture is slowly warmed up and stirred at 20° C. for 1 h. The reaction mixture is diluted with $CH_2Cl_2$ (20 mL), washed with saturated $NaHCO_3$ (3×20 mL) and brine (20 mL), and dried over $Na_2SO_4$. The solvent is removed in vacuo, and the residue is purified via flash chromatography (SiO2, hexane/acetone=4/1) to give the title compound (100 mg).

MS (ESI) m/z 1023.14 $(M+H)^+$

EXAMPLE 2

Compound of formula I, wherein W is —$CH_2CH$=$CHCH_2$—, D=

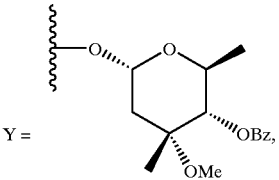

$L=CH_2CH_3$, and $R_2'$=Bz.

A solution of compound from step 1e (100 mg, 0.1 mmol) in 5 ml methanol is added $NaBH_4$ (17 mg, 0.5 mmol) at room temperature. The resulting mixture is stirred at room temperature for 2 hours. Subsequently, Tri(hydroxymethyl) aminomethane (5% in water) (20 ml) is added and stirred vigorously for 1 hour and the mixture is extracted with ethyl acetate (30 ml). The organic phase is dried over Na$_2$SO$_4$ and concentrated. The residue is purified on silica gel to give the title compound (90 mg).

MS (ESI) m/z 995.40 (M+H)$^+$

Compound of formula I, wherein W is —CH$_2$CH=CHCH$_2$—, D=—NHCH$_2$, X=Z=H,

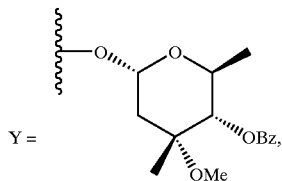

Y =

L=CH$_2$CH$_3$, and R$_2$'=H.

A solution of compound of example 1 (90 mg) in 10 ml methanol is refluxed for 3 hours. The solvent is removed and the residue is purified by flash chromatography (SiO$_2$, 2M ammonia in methanol:CH$_2$Cl$_2$=5:95) to give the title compound (80 mg).

MS (ESI) m/z 891.44 (M+H)$^+$ $^{13}$C NMR(CDCl$_3$): δ177.2, 165.3, 133.8, 132.2, 131.5, 129.1, 128.7, 127.3, 101.9, 94.0, 79.6, 78.6, 78.4, 78.3, 76.2, 72.6, 72.0, 71.7, 70.1, 69.8, 67.2, 64.7, 62.3, 60.8, 57.2, 48.6, 45.1, 43.0, 40.9, 39.4, 33.9, 28.1, 27.9, 21.2, 21.1, 20.7, 20.4, 20.3, 17.3, 17.2, 14.3, 10.3, 8.1.

EXAMPLE 3

Compound of formula I, wherein W is —CH$_2$CH=CHCH$_2$—, D=—NHCH$_2$—, X=Z=H, Y=OH, L=CH$_2$CH$_3$, and R$_2$'=H.

To a solution of the compound from step 1c (18 mg, 0.02 mmol) in 1 ml ethanol is added 2M HCl (1 ml). The mixture is heated to 60° C. and stirred for 3 hours after which to the mixture is added saturated Na$_2$CO$_3$ (10 ml). The resulting mixture is then extracted with ethyl acetate (10 ml), washed with brine (10 ml×2), dried over anhydrous Na$_2$SO$_4$, and concentrated in vacuo. The residue is purified by flash chromatography (SiO$_2$, 2M ammonia in methanol: CH$_2$Cl$_2$= 5:95) to give the title compound (12 mg).

MS (ESI) m/z 629.37(M+H)$^+$.

13C NMR(CDCl$_3$): δ174.5, 127.2, 98.2, 89.4, 86.2, 79.5, 75.4, 74.5, 72.1, 71.6, 69.5, 61.6, 54.5, 52.7, 47.5, 42.3, 40.9, 39.2, 32.1, 29.3, 27.0, 20.9, 20.5, 19.5, 18.5, 17.3, 16.8, 9.8, 9.2.

EXAMPLE 4

Compound of formula I, wherein W is —CH$_2$CH=CHCH$_2$—, D=—NHCH$_2$—, X and Y are taken together with the carbon to which they are attached are C=O, L=CH$_2$CH$_3$, and R$_2$'=H.

To a solution of compound of example 2 (12 mg) in 5 ml dichloromethane is added acetic acid (20 μl) and Dess-Martin reagent (15 mg) at room temperature. The mixture is stirred at room temperature for 30 minutes and Na$_2$S$_2$O$_3$ (20 mg) is added. After stirring for 1 hour, to the mixture is added saturated NaHCO$_3$ (10 ml). The resulting reaction mixture is then extracted with dichloromethane (10 ml), dried over anhydrous Na$_2$SO$_4$. The solvent is removed and the residue is purified by flash chromatography (SiO$_2$, 2M ammonia in methanol:CH$_2$Cl$_2$=5:95) to give the title compound (8 mg). MS (ESI) m/z 627.31 (M+H)$^+$ $^{13}$C NMR(CDCl$_3$): δ211.1, 171.6, 125.8, 97.6, 89.2, 85.6, 79.6, 74.5, 71.5, 70.3, 68.9, 61.2, 55.4, 52.3, 50.6, 46.8, 40.2, 39.8, 38.9, 32.1, 26.5, 21.1, 20.8, 19.5, 18.9, 18.2, 17.5, 9.6, 9.2.

EXAMPLE 5

A compound of formula I, wherein W is —CH$_2$CH=CHCH$_2$, D=—NHC(O)—, X=Z=H, L=—CH$_2$CH$_3$,

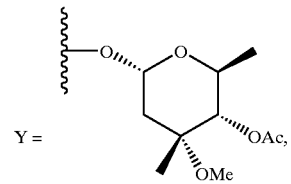

Y =

R$_2$'=H.

Step 5a:

A compound of formula (1-2), wherein R$_2$'=R$_4$"=R$_8$=Ac.

To a solution of erythromycin A oxime (74.9 g, 0.1 mol) in 400 ml THF is added acetic anhydride (35.9 ml, 0.38 mol), triethylamine (55.7 ml, 0.4 mol) and DMAP (3.7 g, 0.03 mol) at room temperature. The mixture is stirred at room temperature for 16 hours, condensed to −200 ml, and diluted with 300 ml of ethyl acetate. The resulting mixture is then washed with NaHCO$_3$ (Sat.) (500 ml×4) and brine (500 ml), and dried on anhydrous Na$_2$SO$_4$. The solvent is evaporated in vacuo and the residue is recrystallized from ethyl acetate to give title compound (78 g).

MS (ESI) m/z 875.46 (M+H)$^+$.

$^{13}$C NMR(CDCl$_3$): δ178.5, 175.4, 170.6, 170.2, 168.2, 100.2, 96.1, 83.3, 79.3, 78.7, 75.2, 74.5, 72.9, 70.0, 67.6, 634, 63.2, 60.6, 49.5, 44.7, 40.9, 35.4, 31.8, 28.5, 22.8, 21.7, 21.6, 21.5, 21.3, 21.2, 21.1, 19.9, 18.6, 18.4, 16.7, 14.9, 14.4, 14.3, 10.8, 9.2.

Step 5b:

A compound of formula (1-4), wherein A=B=H, and R$_2$'=R$_4$"=R$_8$=Ac.

To a solution of erythromycin oxime 2', 4", 9-triacetate from Step 5a (4.38 g, 5 mmol), the compound from step 1b (4.33 g, 15 mmol) and dppb (213 mg, 0.5 mmol) in THF (40 ml), is added Pd$_2$(dba)$_3$ (229 mg, 0.25 mmol) under nitrogen. The mixture is refluxed for 1.5 hours and diluted with ethyl acetate (150 ml). The resulting mixture is then washed with saturated NaHCO$_3$ (200 ml×2) and brine (200 ml), and dried over anhydrous Na$_2$SO$_4$. The solvent is removed in vacuo, and the residue is purified by flash chromatography (SiO$_2$ hexane:acetone/2:1) to give the title compound (4.0 g).

MS (ESI) m/z 927.54 (M+H)$^+$

Step 5c:

A compound of formula (1-4), wherein A=B=H, and R$_2$'=R$_4$"=Ac, and R$_8$=H.

To a solution of compound from step 5b (456 mg, 0.46 mmol) in THF (5 ml) and isopropanol (5 ml) at 0° C. is added 1N LiOH (2.5 ml). The reaction mixture is stirred at 0° C. for 30 minutes and quenched with saturated NaHCO$_3$ (10 ml). The resulting reaction mixture is then extracted with ethyl acetate (15 ml) and the organic layer is dried over anhydrous Na$_2$SO$_4$. The solvent is removed in vacuo, and the residue is purified by flash chromatography (SiO$_2$ hexane:acetone/1:1) to give the title compound (433 mg).

MS (ESI) m/z 885.29 (M+H)+.
13C NMR(CDCl₃): δ176.3, 170.7, 170.2, 165.3, 138.4, 130.4, 100.4, 96.5, 79.8, 79.3, 78.8, 78.3, 75.6, 74.5, 73.0, 72.0, 67.7, 63.3, 63.0, 60.5, 49.6, 45.2, 40.8, 39.6, 35.4, 35.1, 34.9, 31.1, 27.1, 22.9, 21.6, 21.2, 21.1, 21.0, 20.8, 20.4, 18.1, 15.2, 14.3, 11.1, 9.3.

Step 5d:
A compound of formula I, wherein W is —CH₂CH=CHCH₂—, D=—NHC(O)—, X=Z=H, L=—CH₂CH₃,

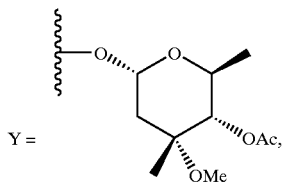

Y =

R₂'=Ac.

To a solution of the compound from step 5c (120 mg, 0.13 mmol) in acetone is added a solution of TsCl (49 mg, 0.27 mmol) in 0.4 ml acetone and a solution of NaHCO₃ (44 mg, 0.52 mmol) in 1.4 ml water at 0° C. The reaction mixture is stirred at 0° C. for 2 hours and then warmed to room temperature overnight. The reaction mixture is then diluted with 15 ml methylene chloride, washed with brine (20 ml×2), and dried over Na₂SO₄. The solvent is subsequently removed in vacuo and the residue is purified by flash chromatography (SiO₂, hexane/acetone=1/1) to give the title compound (70 mg).

MS (ESI) m/z 885.44(M+H)+
13C NMR(CDCl₃): δ178.9, 176.8, 170.8, 170.2, 135.7, 131.9, 100.6, 94.5, 79.9, 79.1, 78.7, 78.5, 76.3, 75.1, 74.3, 73.1, 72.0, 70.8, 67.6, 63.4, 62.9, 61.5, 49.6, 45.7, 45.5, 42.5, 40.9, 39.5, 37.2, 35.1, 31.7, 31.1, 29.4, 22.0, 21.7, 21.6, 21.5, 21.4, 21.1, 20.9, 18.3, 15.1, 14.5, 11.3, 9.3.

Step 5e:
Title compound:
A solution of compound of example 5d (60 mg) in 5 ml methanol is refluxed for 3 hours. The solvent is removed and the residue is purified by flash chromatography (SiO₂, 2M ammonia in methanol:CH₂Cl₂=5:95) to give the title compound (50 mg).

MS (ESI) m/z 843.32(M+H)+

EXAMPLE 6

A compound of formula I, wherein W is —CH₂CH=CHCH₂—, D=—N(Q)CH₂—, Q=CH, X=Z=H, Y=OH, L=CH₂CH₃, R₂'=H.

To a solution of the compound of Example 3 (63 mg, 0.1 mmol) in 10 ml methanol is added formaldehyde (37% in water) (100 µl), acetic acid (100 µl) and NaCNBH₃ (50 mg) at room temperature. The mixture is stirred at room temperature for 4 hours after which is added 5% Tris (30 ml). After stirring vigorously for 1 hour, the mixture is extracted with ethyl acetate (40 ml) and dried over anhydrous Na₂SO₄. The solvent is removed in vacuo and the residue is purified by flash chromatography (SiO₂, 2M ammonia in methanol:CH₂Cl₂=5:95) to give the title compound (60 mg).

EXAMPLE 7

A compound of formula I, wherein W is —CH₂CH=CHCH₂—, D=—N(Q)CH₂—, Q=CH₃, Z=H, X and Y taken together are oxo, L=CH₂CH₃, R₂'=H.

The title compound is prepared with the title compound of Example 6 via the Dess-Martin oxidation conditions described in Example 4.

EXAMPLE 8

A compound of formula I, wherein W is CH₂CH=CHCH₂—, D=—N(Q)CH₂—, Q=CH₂Ph, Z=X=H, Y=OH, L=CH₂CH₃, R₂'=H.

A solution of the compound of Example 3 in MeOH is treated with benzaldehyde, excess NaCNBH₃, and acetic acid at room temperature. The reaction mixture is stirred at room temperature for 4–8 hours and subsequently cooled to 0° C. The solution is then neutralized with aqueous NaHCO₃, extracted with methylene chloride, and the organic phase is dried over Na₂SO₄. The solvents are removed in vacuo and the residue is purified via column chromatography on silica gel to provide the title compound.

EXAMPLE 9

A compound of formula I, wherein W is CH₂CH=CHCH₂—, D=—N(Q)CH₂, Q=CH₂Ph, Z=H, X and Y are taken together are oxo, L=CH₂CH₃, R₂'=H.

The title compound is prepared with the title compound of Example 8 via the Dess-Martin oxidation conditions described in Example 4.

EXAMPLE 10

A compound of formula I, wherein W is —CH₂CH=CHCH₂—, D=—N(Q)CH₂—, Q=CH₂(2-pyridyl), Z=X=H, Y=OH, L=CH₂CH₃, R₂'=H.

The title compound is prepared via the procedure set forth in Example 8 with the title compound of Example 3 and 2-pyridine carboxaldehyde.

EXAMPLE 11

A compound of formula I, W is —CH₂CH=CHCH, D=—N(Q)CH₂—, Q=CH₂(2-pyridyl), Z=H, X and Y taken together are oxo, L=CH₂CH₃, R₂'=H.

The title compound is prepared with the title compound of Example 10 via the Dess-Martin oxidation conditions described in Example 4.

EXAMPLE 12

A compound of formula I, wherein W is —CH₂CH=CHCH₂—, D=—N(Q)CH₂—, Q=CH₂(3-quinolyl), Z=H, X and Y taken together are oxo, L=CH₂CH, R₂'=H.

The title compound is prepared via the procedure set forth in Example 8 with the title compound of Example 3 and 3-quinoline carboxaldehyde.

EXAMPLE 13

A compound of formula I, wherein W is —CH₂CH=CHCH₂, D=—N(Q)CH₂—, Q=CH₂(3-quinolyl), Z=H, X and Y taken together are oxo, L=CH₂CH₃, R₂'=H.

The title compound is prepared with the title compound of Example 12 via the Dess-Martin oxidation conditions described in Example 4.

EXAMPLE 14

A compound of formula I, wherein W is —CH₂CH=CHCH₂—, D=—N(Q)CH₂—, Q=CH₂(CH=CH)Ph, Z=X=H, Y=OH, L=CH₂CH₃, R₂'H.

The title compound is prepared via the procedure set forth in Example 8 with the title compound of Example 3 and cinnamaldehyde.

EXAMPLE 15

A compound of formula I, wherein W is —CH$_2$CH=CHCH$_2$—, D=—N(Q)CH$_2$—, Q=CH$_2$(CH=CH)Ph, Z=H, X and Y taken together are oxo, L=CH$_2$CH$_3$, R$_2$'=H.

The title compound is prepared with the title compound of Example 14 via the Dess-Martin oxidation conditions described in Example 4.

EXAMPLE 16

A compound of formula I, wherein W is —CH$_2$CH=CHCH$_2$—, D=—N(Q)CH$_2$—, Q=CH$_2$CH=CH(2-pyridyl), Z=X=H, Y=OH, L=CH$_2$CH$_3$, R$_2$'=H.

The title compound is prepared via the procedure set forth in Example 8 with the title compound of Example 3 and 3-(2-pyridyl)acrolein.

EXAMPLE 17

A compound of formula I, wherein A and B taken together with the carbon atom to which they are attached=C=CH$_2$, D=—N(Q)CH$_2$—, Q=CH$_2$CH=CH(2-pyridyl), Z=H, X and Y taken together are oxo, L=CH$_2$CH$_3$, R$_2$'=H.

The title compound is prepared with the title compound of Example 16 via the Dess-Martin oxidation conditions described in Example 4.

EXAMPLE 18

A compound of formula I, wherein W is —CH$_2$CH=CHCH$_2$—, D=—N(Q)CH$_2$—, Q=CH$_2$C≡C(3-quinolyl), Z=X=H, Y=OH, L=CH$_2$CH$_3$, R$_2$'=H.

The title compound is prepared via the procedure set forth in Example 8 with the title compound of Example 3 2 and 3-(3-quinolyl)propynaldehyde.

EXAMPLE 19

A compound of formula I, wherein W=—CH$_2$CH=CHCH$_2$—, D=—N(Q)CH$_2$—, Q=CH$_2$C≡C(3-quinolyl), Z=H, X and Y taken together are oxo, L=CH$_2$CH$_3$, R$_2$'=H.

The title compound is prepared with the title compound of Example 18 via the Dess-Martin oxidation conditions described in Example 4.

Although the invention has been described with respect to various preferred embodiments, it is not intended to be limited thereto, but rather those skilled in the art will recognize that variations and modifications may be made therein which are within the spirit of the invention and the scope of the appended claims.

What is claimed:
1. A compound of formula I, or a pharmaceutically acceptable salt, ester, or prodrug thereof:

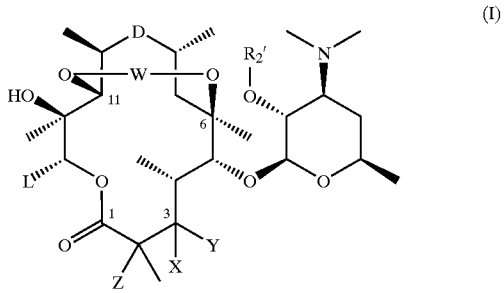

(I)

wherein:
W is
(a) —CH$_2$—C(A)=C(B)—CH$_2$—, wherein, A and B are independently selected from:
1. hydrogen;
2. deuterium;
3. halogen;
4. R$_1$, wherein R$_1$ is selected from:
    a. —C$_1$-C$_6$ alkyl, optionally substituted with one or more substituents selected from halogen, aryl, substituted aryl, heteroaryl, or substituted heteroaryl;
    b. —C$_2$-C$_6$ alkenyl, optionally substituted with one or more substituents selected from halogen, aryl, substituted aryl, heteroaryl, or substituted heteroaryl; or
    c. —C$_2$-C$_6$ alkynyl, optionally substituted with one or more substituents selected from halogen, aryl, substituted aryl, heteroaryl, or substituted heteroaryl;
5. R$_2$, wherein R$_2$ is selected from:
    a. aryl;
    b. heteroaryl;
    c. substituted aryl;
    d. substituted heteroaryl;
    e. heterocycloalkyl; or
    f. substituted heterocycloalkyl;
6. —(C$_1$-C$_3$-alkyl)-M—(C$_1$-C$_3$-alkyl)-R$_2$, wherein M is selected from —O—, —NH—, —N(CH$_3$)—, —NHC(O)— or —S(O)$_n$—, wherein n=0, 1 or 2, and R$_2$ is as previously defined:
7. —(C$_1$-C$_3$-alkyl)-M—R$_2$, wherein M and R$_2$ are as previously defined;
8. —C(O)—V—R$_3$, wherein V is absent, O or S, and R$_3$ is H, R$_1$ or R$_2$; where R$_1$ and R$_2$ are as previously defined; or
9. —(O)—NR$_{11}$R$_{12}$, wherein R$_{11}$ and R$_{12}$ are each independently selected from:
    a. hydrogen;
    b. —C$_1$-C$_6$-alkyl, optionally substituted with one or more substituents selected from halogen, aryl, substituted aryl, heteroaryl, or substituted heteroaryl;
    c. —C$_2$-C$_6$-alkenyl, optionally substituted with one or more substituents selected from halogen, aryl, substituted aryl, heteroaryl, or substituted heteroaryl;
    d. —C$_2$-C$_6$-alkynyl, optionally substituted with one or more substituents selected from halogen, aryl, substituted aryl, heteroaryl, or substituted heteroaryl; or
    in the alternative, R$_{11}$ and R$_{12}$ taken together with the nitrogen atom to which they are connected form a 3-to 7-membered ring which may optionally contain one or more double bonds and one or more heterofunctions selected from —O—, —NH—, —N($C_1$-$C_6$-alkyl)-, —N($R_2$)—, —S(O)$_n$—, wherein n and $R_2$ are as previously defined;

(b) —$CH_2$—CH(A)—C(B)=CH—, wherein A and B are as previously defined;

(c) —$CH_2$—CH(E)—CH(G)—$CH_2$—, wherein E and G are independently selected from
1. A, wherein A is as previously defined;
2. —OH;
3. —OR$^p$, wherein R$^p$ is a hydroxy protecting group;
4. —O—$R_9$, wherein $R_9$ is $R_1$ or $R_2$, and wherein $R_1$ and $R_2$ are as previously defined;
5. —S(O)$_n$$R_9$, wherein n and $R_9$ are as previously defined;
6. —NHC(O)$R_3$, wherein $R_3$ is as previously defined;
7. —NHC(O)N$R_{11}$$R_3$, wherein $R_{11}$ and $R_3$ are as previously defined;
8. —NHS(O)$_2$$R_9$, wherein $R_9$ is as previously defined;
9. —NH$R_{13}$, wherein $R_{13}$ is an amino protecting group; or
10. —N$R_{11}$$R_{12}$, wherein $R_{11}$, and $R_{12}$ are as previously defined;

(d)

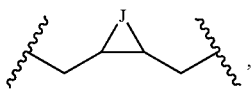

wherein —J— is selected from —O—; —O—C(O)—CH($R_7$)—; —N($R_7$)—; —O—C(O)—N($R_7$)—; —O—C(O)—O—; —N($R_7$)—N=N—; —C($R_7$)=N—O—; or —CH($R_7$)—N($R_8$)—O—; wherein $R_7$ and $R_8$ are independently selected from $R_3$, wherein $R_3$ is as previously defined; or, in the alternative, —J— is taken with the two carbon atoms to which it is attached to form a cyclic moiety selected from
a. $C_3$–$C_{12}$ cycloalkyl;
b. $C_3$–$C_{12}$ cycloalkenyl; or
c. heterocycloalkyl; or (e) —$CH_2$—C($R_4$)($R_5$)—$CH_2$—$CH_2$—, wherein $R_4$ and $R_5$ taken together with the carbon atom to which they are attached are selected from:
1. C=O;
2. C(O$R_1$)$_2$, wherein $R_1$ is as previously defined;
3. C(S$R_1$)$_2$, wherein $R_1$ is as previously defined;
4. C(O$R_{12}$)(O$R_{13}$), where $R_{12}$ and $R_{13}$ taken together are —(CH$_2$)$_m$—, and where m is 2 or 3;
5. C(S$R_{12}$)(S$R_{13}$), where $R_{12}$ and $R_{13}$ taken together are —(CH$_2$)$_m$—, where m is as previously defined;
6. C=CH$R_3$, wherein $R_3$ is as previously defined;
7. C=N—O—$R_3$, wherein $R_3$ is as previously defined;
8. C=NNH$R_3$, wherein $R_3$ is as previously defined;
9. C=NNHC(O)$R_3$, wherein $R_3$ is as previously defined;
10. C=NNNHC(O)N$R_{11}$$R_3$, wherein $R_{11}$ and $R_3$ are as previously defined;
11. C=NNHS(O)$_2$$R_9$, wherein $R_9$ is as previously defined;
12. C=NNH$R_{13}$, wherein $R_{13}$ is as previously defined; or
13. C=N$R_9$, wherein $R_9$ is as previously defined;

L is
(a) —$CH_3$;
(b) —$CH_2$$CH_3$;
(c) —CH(OH)$CH_3$;
(d) —$C_1$–$C_6$-alkyl, optionally substituted with one or more substituents selected from aryl, substituted aryl, heteroaryl, or substituted heteroaryl;
(e) —$C_2$–$C_6$ alkenyl, optionally substituted with one or more substituents selected from aryl, substituted aryl, heteroaryl, or substituted heteroaryl; or
(f) —$C_2$–$C_6$alkynyl, optionally substituted with one or more substituents selected from aryl, substituted aryl, heteroaryl, or substituted heteroaryl;

D is —N(Q)CH$_2$—, N(R')C(O)—, or —N=C(OR')—, wherein R' is $R_{11}$ as previously defined;

Q is
(a) hydrogen;
(b) —$C_1$–$C_{12}$-alkyl, $C_2$–$C_{12}$-alkenyl, or $C_2$–$C_{12}$-alkynyl, all optionally substituted with one, two or three substituents independently selected from:
1. halogen;
2. —O$R_6$, wherein $R_6$ is selected from:
a. hydrogen;
b. —$C_1$–$C_{12}$-alkyl containing 0, 1, 2, or 3 heteroatoms selected from O, S or N, optionally substituted with one, two, or three substituents independently selected from aryl, substituted aryl, heteroaryl, or substituted heteroaryl;
c. aryl;
d. substituted aryl;
e. heteroaryl;
f. substituted heteroaryl;
g. heterocycloalkyl; or
h. substituted heterocycloalkyl;
3. —N$R_4$$R_5$, where $R_4$ and $R_5$ are each independently $R_6$, where $R_6$ is as previously defined, or in the alternative $R_4$ and $R_5$, together with the atom to which they are attached, form a heterocycloalkyl or substituted heterocycloalkyl moiety;
4. =N—O—$R_6$, where $R_6$ is as previously defined;
5. —$R_1$, where $R_1$ is as previously defined;
6. —$C_3$–$C_8$-cycloalkyl;
7. substituted —$C_3$–$C_8$-cycloalkyl;
8. heterocycloalkyl;
9. substituted heterocycloalkyl;
10. —NHC(O)$R_6$, where $R_6$ is as previously defined;
11. —NHC(O)O$R_7$, where $R_7$ is selected from:
a. —$C_1$–$C_{12}$-alkyl containing 0, 1, 2, or 3 heteroatoms selected from O, S or N, optionally substituted with one, two, or three substituents independently selected from aryl, substituted aryl, heteroaryl, or substituted heteroaryl;
b. aryl;
c. substituted aryl;
d. heteroaryl;
e. substituted heteroaryl;
f. heterocycloalkyl; or
g. substituted heterocycloalkyl;
12. —NHC(O)N$R_4$$R_5$, where $R_4$ and $R_5$ are as previously defined;
13. —OC(O)N$R_4$$R_5$, where $R_4$ and $R_5$ are as previously defined;
14. —OC(O)$R_7$, where $R_7$ is as previously defined;
15. —OC(O)O$R_7$, where $R_7$ is as previously defined;

16. —OC(O)NR$_4$R$_5$, where R$_4$ and R$_5$ are as previously defined,

17. —C(O)R$_6$, where R$_6$ is as previously defined,

18. —CO$_2$R$_6$, where R$_6$ is as previously defined, or

19. —C(O)NR$_4$R$_5$, where R$_4$ and R$_5$ are as previously defined;

X is hydrogen;

Y is
(a) hydrogen;
(b) —OH;
(c) —OR$_p$, where R$_p$ is as previously defined;
(d) —OR$_y$, where R$_y$ is R$_1$ and R$_2$ as previously defined;
(e) —OC(O)R$_y$, where R$_y$ is R$_1$ and R$_2$ as previously defined;
(f) —OC(O)NHR$_y$, where R$_y$ is R$_1$ and R$_2$ as previously defined;
(g) —S(O)$_n$R$_y$, where n is previously defined and R$_y$ is R$_1$ and R$_2$ as previously defined;
(h) —

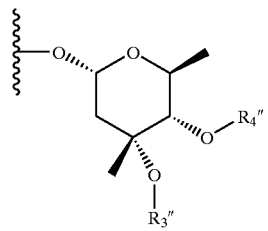

where R$_3$" is hydrogen or methyl; R$_4$" is hydrogen or R$_p$, where R$_p$ is as previously defined; or (i) in the alternative, X and Y combined together are oxo;

Z is
(a) hydrogen;
(b) methyl; or
(c) halogen; and

R$_2$' is hydrogen or R$_p$, where R$_p$, is as previously defined.

2. A compound according to claim 1 represented by formula II:

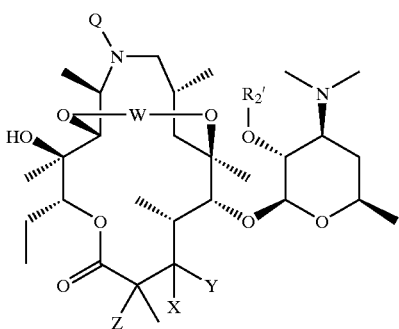

(II)

3. A compound according to claim 1 represented by formula III:

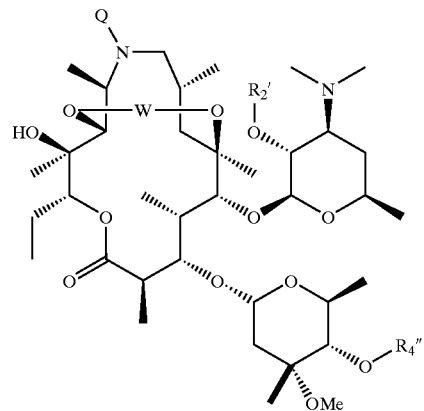

(III)

4. A compound according to claim 1 represented by formula IV:

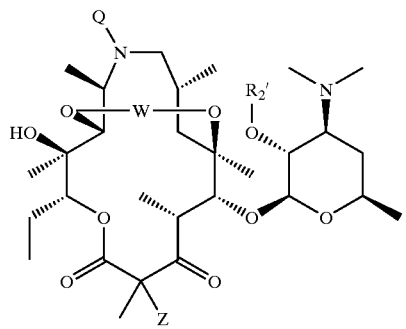

(IV)

5. A pharmaceutical composition comprising a therapeutically effective amount of a compound of claim 1 or a pharmaceutically acceptable salt, ester or prodrug thereof, in combination with a pharmaceutically acceptable carrier.

6. A method for controlling a bacterial infection in a subject, comprising administering to said subject a therapeutically effective amount of a pharmaceutical composition according to claim 5.

7. A process for the preparation of a compound of formula:

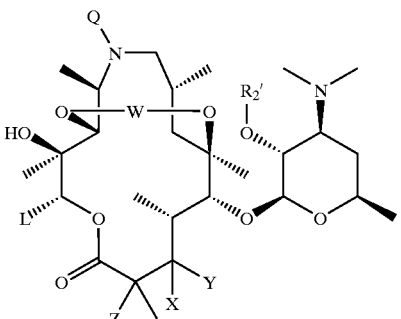

(II)

wherein L, Q, W, X, Y, Z and R$_2$' are as defined in claim 1, comprising the steps of:

(1) reacting a compound of the formula:

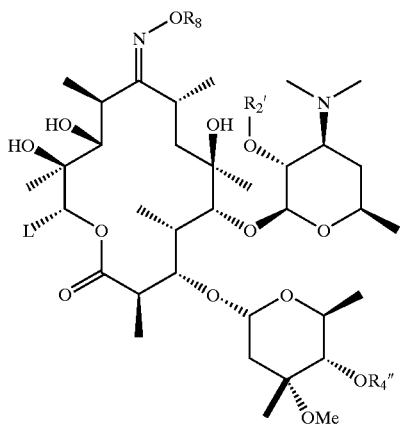

wherein
$R^8$ is
a. Hydrogen;
b. —$CH_2O(CH_2)_2OCH_3$;
c. —$CH_2O(CH_2O)_nCH_3$, where n is as previously defined;
d. —$C_1$–$C_{12}$ alkyl, optionally substituted with one or more substituents selected from aryl, substituted aryl, heteroaryl and substituted heteroaryl;
e. —$C_3$–$C_{12}$ cycloalkyl;
f. —C(O)—$C_1$–$C_{12}$ alkyl;
g. —C(O)—$C_3$–$C_{12}$ cycloalkyl;
h. —C(O)—$R_1$, where $R_1$ is as previously defined; or
i. —Si($R_a$)($R_b$)($R_c$), wherein $R_a$, $R_b$ and $R_c$ are each independently selected from $C_1$–$C_{12}$ alkyl; aryl, or substituted aryl; and
L, $R_2'$, and $R_4''$ are as defined in claim 1;
with

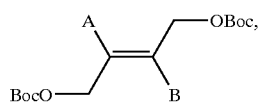

wherein A and B are as defined in claim 1, in the presence of a phosphine ligand and Pd(O) catalyst under reflux conditions to prepare a compound of the formula:

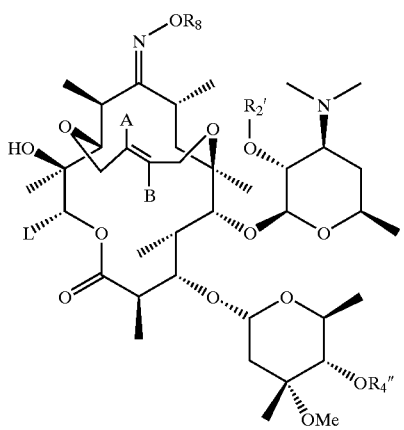

wherein A, B, L, $R_8$, $R_2'$, and $R_4''$ are as defined in claim 1;

(2) reacting the compound prepared in step (1) with a mild acid to prepare a compound of the formula:

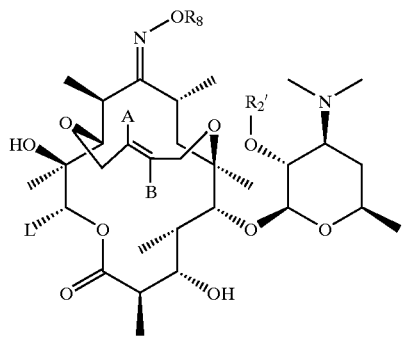

wherein A, B, L, $R_8$, and $R_2'$ are as defined in claim 1;

(3) reacting the compound prepared in step (2) with an oxime activating agent and quenching with methanol to prepare a compound of the formula:

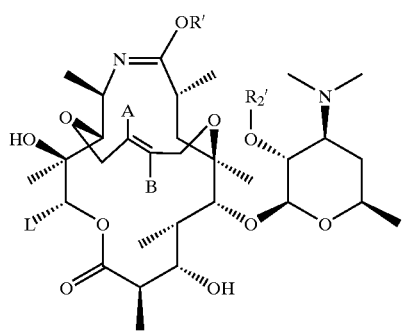

wherein A, B, L, R', and $R_2'$ are as defined claim 1;

(4) reacting the compound prepared in step (3) with a reducing agent to prepare compound of the formula:

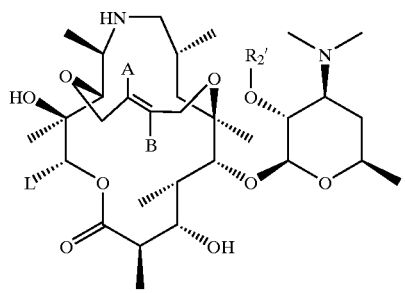

wherein A, B, L, and $R_2'$ are as defined claim 1;

(5) reacting the compound prepared in step (4) with an alkylating agent, preferably an alykyl halide in the presence of a base, or with an aldehyde via reductive amination in the presence of $NaCNBH_3$ to prepare a compound of the formula:

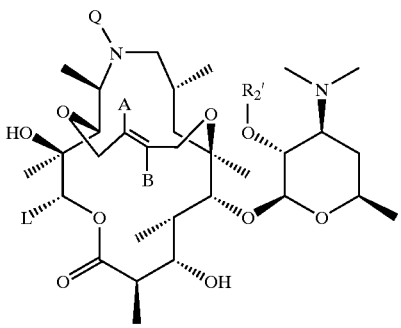

wherein A, B, L, Q, and R$_2$' is as defined claim 1; and
(6) oxidizing the hydroxyl in the 3 position of the compound prepared in step (5) via Dess-Martin oxidation, Corey-Kim oxidation, or a Moffat oxidation to prepare a compound of the formula:

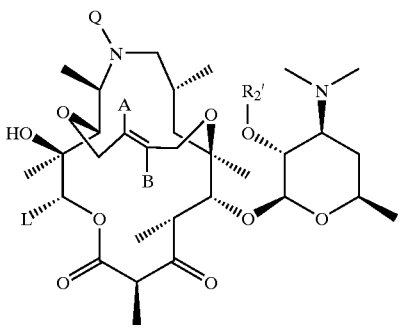

wherein A, B, L, Q, and R$_2$' are as defined claim 1.

8. A compound of claim 1 selected from:

Compound of formula I, wherein W is —CH$_2$CH=CHCH$_2$—, D is —N=CH(OMe)—, X is H, Z is H, Y is

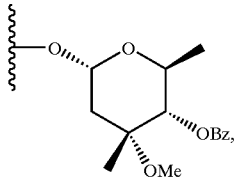

L is CH$_2$CH$_3$, and R$_2$' is Bz;

Compound of formula I, wherein W is —CH$_2$CH=CHCH$_2$—, D is —NHCH$_2$—, X is H, Z is H, Y is

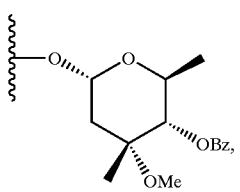

L is CH$_2$CH$_3$, and R$_2$' is Bz;

Compound of formula I, wherein W is —CH$_2$CH=CHCH$_2$—, D is —NHCH$_2$—, X is H, Z is H, Y is

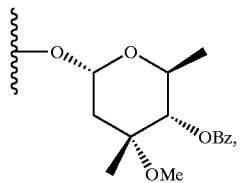

L is CH$_2$CH$_3$, and R$_2$' is H;

Compound of formula I, wherein W is —CH$_2$CH=CHCH$_2$—, D is —NHCH$_2$—, X is H, Z is H, Y is OH, L is CH$_2$CH$_3$, and R$_2$' is H;

Compound of formula I, wherein W is —CH$_2$CH=CHCH$_2$—, D is —NHCH$_2$—, X and Y are taken together with the carbon to which they are attached are C=O, L is CH$_2$CH$_3$, and R$_2$' is H;

A compound of formula I, wherein W is —CH$_2$CH=CHCH$_2$—, D is —NHC(O)—, X is H, Z is H, L is —CH$_2$CH$_3$, Y is

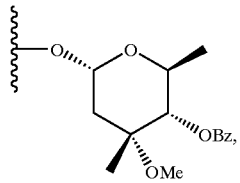

R$_2$' is H;

A compound of formula I, wherein W is —CH$_2$CH=CHCH$_2$—, D is —N(Q)CH$_2$—, Q is CH$_3$, X is H, Z is H, Y is OH, L is CH$_2$CH$_3$, R$_2$' is H;

A compound of formula I, wherein W is —CH$_2$CH=CHCH$_2$—, D is —N(Q)CH$_2$—, Q is CH$_3$, Z is H, X and Y taken together are oxo, L is CH$_2$CH$_3$, R$_2$' is H;

A compound of formula I, wherein W is —CH$_2$CH=CHCH$_2$—, D is —N(Q)CH$_2$—, Q is CH$_2$Ph, Z is H, X is H, Y is OH, L is CH$_2$CH$_3$, R$_2$' is H;

A compound of formula I, wherein W is —CH$_2$CH=CHCH$_2$—, D is —N(Q)CH$_2$—, Q is CH$_2$Ph, Z is H, X and Y are taken together are oxo, L is CH$_2$CH$_3$, R$_2$' is H;

A compound of formula I, wherein W is —CH$_2$CH=CHCH$_2$—, D is —N(Q)CH$_2$—, Q is CH$_2$(2-pyridyl), Z is H, X is H, Y is OH, L is —CH$_2$CH$_3$, R$_2$' is H;

A compound of formula I, W is —CH$_2$CH=CHCH$_2$—, D is —N(Q)CH$_2$—, Q is CH$_2$(2-pyridyl), Z is H, X and Y taken together are oxo, L is CH$_2$CH$_3$, R$_2$' is H;

A compound of formula I, wherein W is —CH$_2$CH=CHCH$_2$—, D is —N(Q)CH$_2$—, Q is CH$_2$(3-quinolyl), Z is H, X and Y taken together are oxo, L is CH$_2$CH$_3$, R$_2$' is H;

A compound of formula I, wherein W is —CH$_2$CH=CHCH$_2$—, D is —N(Q)CH$_2$—, Q is CH$_2$(3-quinolyl), Z is H, X and Y taken together are oxo, L is CH$_2$CH$_3$, R$_2$' is H;

A compound of formula I, wherein W is —CH$_2$CH=CHCH$_2$—, D is —N(Q)CH$_2$—, Q is CH$_2$(CH=CH)Ph, Z is H, X is H, Y is OH, L is CH$_2$CH$_3$, R$_2$' is H;

A compound of formula I, wherein W is —CH$_2$CH=CHCH$_2$—, D is —N(Q)CH$_2$—, Q is CH$_2$(CH=CH)Ph, Z is H, X and Y taken together are oxo, L is CH$_2$CH$_3$, R$_2$' is H;

A compound of formula I, wherein W is —CH$_2$CH=CHCH$_2$, D is —N(Q)CH$_2$—, Q is CH$_2$CH=CH(2-pyridyl), Z is H, X is H, Y is OH, L is CH$_2$CH$_3$, R$_2$' is H;

A compound of formula I, wherein A and B taken together with the carbon atom to which they are attached are C=CH$_2$, D is —N(Q)CH$_2$—, Q is CH$_2$CH=CH(2-pyridyl), Z is H, X and Y taken together are oxo, L is CH$_2$CH$_3$, R$_2$' is H;

A compound of formula I, wherein W is —CH$_2$CH=CHCH$_2$—, D is —N(Q)CH$_2$—, Q is CH$_2$C≡C(3-quinolyl), Z is H, X is H, Y is OH, L is CH$_2$CH$_3$, R$_2$' is H; or A compound of formula I, wherein W is —CH$_2$CH=CHCH$_2$—, D is —N(Q)CH$_2$—, Q is CH$_2$C≡C(3quinolyl), Z is H, X and Y taken together are oxo, L is CH$_2$CH$_3$, R$_2$' is H.

* * * * *

UNITED STATES PATENT AND TRADEMARK OFFICE
CERTIFICATE OF CORRECTION

PATENT NO.   : 6,764,998 B1
DATED        : July 20, 2004
INVENTOR(S)  : Guoqiang Wang, Yat Sun Or and Ly Tam Phan It is certified that error appears in the above-identified patent and that said Letters Patent is hereby corrected as shown below:

Column 58,
Line 50, delete "–(O)" and insert -- - C(O) --.

Column 59,
Line 64, delete "C = NNNHC(O)NR$_{11}$R$_3$" and insert -- C = NNHC(O)NR$_{11}$R$_3$ --.

Signed and Sealed this

Thirtieth Day of November, 2004

JON W. DUDAS
*Director of the United States Patent and Trademark Office*